(12) United States Patent
Fourkas et al.

(10) Patent No.: US 10,213,244 B2
(45) Date of Patent: Feb. 26, 2019

(54) CRYOGENIC NEEDLE WITH FREEZE ZONE REGULATION

(71) Applicant: MyoScience, Inc., Fremont, CA (US)

(72) Inventors: Michael Fourkas, Sunnyvale, CA (US); Ronald Williams, Menlo Park, CA (US); John Allison, Los Altos, CA (US); Jesse Rosen, Albany, CA (US)

(73) Assignee: Myoscience, Inc., Fremont, CA (US)

( * ) Notice: Subject to any disclaimer, the term of this patent is extended or adjusted under 35 U.S.C. 154(b) by 322 days.

(21) Appl. No.: 15/065,685

(22) Filed: Mar. 9, 2016

(65) Prior Publication Data

US 2016/0183998 A1 Jun. 30, 2016

Related U.S. Application Data

(62) Division of application No. 13/741,360, filed on Jan. 14, 2013, now Pat. No. 9,314,290.

(Continued)

(51) Int. Cl.
*A61B 18/02* (2006.01)
*A61B 18/00* (2006.01)
*A61B 17/00* (2006.01)

(52) U.S. Cl.
CPC .... *A61B 18/02* (2013.01); *A61B 2017/00473* (2013.01); *A61B 2018/00029* (2013.01); *A61B 2018/00041* (2013.01); *A61B 2018/00648* (2013.01); *A61B 2018/00714* (2013.01); *A61B 2018/00738* (2013.01); *A61B 2018/00898* (2013.01); *A61B 2018/00994* (2013.01);
(Continued)

(58) Field of Classification Search
CPC ........... A61B 2018/00041; A61B 2018/00023; A61B 2018/0281; A61B 2018/0287; A61B 2018/0293; A61B 18/02; A61B 18/0206; A61B 2018/0212; A61B 18/0218; A61B 2018/0225; A61B 2018/0231; A61B 2018/0237; A61B 2018/0243; A61B 2018/025; A61B 2018/0256; A61B 2018/0262; A61B 2018/0268

See application file for complete search history.

(56) References Cited

U.S. PATENT DOCUMENTS 2,319,542 A 5/1943 Hall
2,672,032 A 3/1964 Towse
(Continued)

FOREIGN PATENT DOCUMENTS

CA 2643474 9/2007
EP 43447 1/1982
(Continued)

OTHER PUBLICATIONS

"Cryoablation in Pain Management brochure", Metrum CryoFlex, 2012, 5 pages.
(Continued)

*Primary Examiner* — Jaymi Della
(74) *Attorney, Agent, or Firm* — Kilpatrick Townsend & Stockton LLP

(57) ABSTRACT

A cryogenic needle of a cryogenic system is coupled to a heater. While the needle is inserted into target tissue beneath skin, the heater provides heat to protect the skin. Power supplied to the heater is used to interpolate performance of the needle and/or operating parameters of the cryogenic system.

23 Claims, 9 Drawing Sheets

Related U.S. Application Data

(60) Provisional application No. 61/586,694, filed on Jan. 13, 2012.

(52) U.S. Cl.
CPC ............ *A61B 2018/0262* (2013.01); *A61B 2018/0293* (2013.01)

(56) References Cited

U.S. PATENT DOCUMENTS

| | | |
|---|---|---|
| 3,266,492 A | 8/1966 | Steinberg |
| 3,289,424 A | 12/1966 | Shepherd |
| 3,343,544 A | 9/1967 | Dunn et al. |
| 3,351,063 A | 11/1967 | Malaker et al. |
| 3,439,680 A | 4/1969 | Thomas, Jr. |
| 3,483,869 A | 12/1969 | Hayhurst |
| 3,502,081 A | 3/1970 | Amoils |
| 3,507,283 A | 4/1970 | Thomas, Jr. |
| 3,532,094 A | 10/1970 | Stahl |
| 3,664,344 A | 5/1972 | Bryne |
| 3,702,114 A | 11/1972 | Zacarian |
| 3,795,245 A | 3/1974 | Allen, Jr. et al. |
| 3,814,095 A | 6/1974 | Lubens |
| 3,830,239 A | 8/1974 | Stumpf et al. |
| 3,886,945 A | 6/1975 | Stumpf et al. |
| 3,889,681 A | 6/1975 | Waller et al. |
| 3,951,152 A | 4/1976 | Crandell et al. |
| 3,993,075 A | 11/1976 | Lisenbee et al. |
| 4,140,109 A | 2/1979 | Savic et al. |
| 4,207,897 A | 6/1980 | Lloyd et al. |
| 4,236,518 A | 12/1980 | Floyd |
| 4,306,568 A | 12/1981 | Torre |
| 4,376,376 A | 3/1983 | Gregory |
| 4,404,862 A | 9/1983 | Harris, Sr. |
| 4,524,771 A | 6/1985 | McGregor et al. |
| 4,758,217 A | 7/1988 | Gueret |
| 4,802,475 A | 2/1989 | Weshahy |
| 4,946,460 A * | 8/1990 | Merry .................. A61B 18/02 606/21 |
| 5,059,197 A | 10/1991 | Urie et al. |
| 5,200,170 A | 4/1993 | McDow |
| 5,294,325 A | 3/1994 | Liu |
| 5,324,286 A * | 6/1994 | Fowle .................. A61B 18/02 606/20 |
| 5,334,181 A | 8/1994 | Rubinsky et al. |
| 5,520,681 A | 5/1996 | Fuller et al. |
| 5,571,147 A | 11/1996 | Sluijter et al. |
| 5,647,868 A | 7/1997 | Chinn |
| 5,747,777 A | 5/1998 | Matsuoka |
| 5,755,753 A | 5/1998 | Knowlton |
| 5,814,040 A | 9/1998 | Nelson et al. |
| 5,860,970 A | 1/1999 | Goddard et al. |
| 5,860,971 A | 1/1999 | Clarke |
| 5,879,378 A | 3/1999 | Usui |
| 5,899,897 A * | 5/1999 | Rabin .................. A61B 18/02 606/21 |
| 5,906,612 A * | 5/1999 | Chinn .................. A61B 18/02 606/20 |
| 5,916,212 A | 6/1999 | Baust et al. |
| 5,976,505 A | 11/1999 | Henderson |
| 6,003,539 A | 12/1999 | Yoshihara |
| 6,032,675 A | 3/2000 | Rubinsky |
| 6,039,730 A | 3/2000 | Rabin et al. |
| 6,041,787 A | 3/2000 | Rubinsky |
| 6,139,545 A | 10/2000 | Utley et al. |
| 6,141,985 A | 11/2000 | Cluzeau et al. |
| 6,142,991 A | 11/2000 | Schatzberger |
| 6,182,666 B1 * | 2/2001 | Dobak, III ............ A61B 18/02 128/898 |
| 6,196,839 B1 | 3/2001 | Ross |
| 6,238,386 B1 | 5/2001 | Müller et al. |
| 6,277,099 B1 | 8/2001 | Strowe et al. |
| 6,277,116 B1 | 8/2001 | Utely et al. |
| 6,363,730 B1 | 4/2002 | Thomas et al. |
| 6,371,943 B1 | 4/2002 | Racz et al. |
| 6,432,102 B2 | 8/2002 | Joye et al. |
| 6,494,844 B1 | 12/2002 | Van Bladel et al. |
| 6,503,246 B1 | 1/2003 | Har-shai et al. |
| 6,506,796 B1 | 1/2003 | Fesus et al. |
| 6,546,935 B2 | 4/2003 | Hooven |
| 6,551,309 B1 | 4/2003 | LePivert |
| 6,562,030 B1 | 5/2003 | Abboud et al. |
| 6,648,880 B2 | 11/2003 | Chauvet et al. |
| 6,669,688 B2 | 12/2003 | Svaasand et al. |
| 6,672,095 B1 | 1/2004 | Luo |
| 6,682,501 B1 | 1/2004 | Nelson et al. |
| 6,706,037 B2 | 3/2004 | Zvuloni et al. |
| 6,723,092 B2 | 4/2004 | Brown et al. |
| 6,749,624 B2 | 6/2004 | Knowlton |
| 6,761,715 B2 | 7/2004 | Carroll |
| 6,764,493 B1 | 7/2004 | Weber et al. |
| 6,786,901 B2 | 9/2004 | Joye et al. |
| 6,786,902 B1 | 9/2004 | Rabin et al. |
| 6,789,545 B2 | 9/2004 | Littrup et al. |
| 6,840,935 B2 | 1/2005 | Lee |
| 6,858,025 B2 | 2/2005 | Maurice |
| 6,902,554 B2 | 6/2005 | Huttner |
| 6,905,492 B2 | 6/2005 | Zvuloni et al. |
| 6,960,208 B2 | 11/2005 | Bourne et al. |
| 7,001,400 B1 | 2/2006 | Modesitt et al. |
| 7,081,111 B2 | 7/2006 | Svaasand et al. |
| 7,081,112 B2 | 7/2006 | Joye et al. |
| 7,083,612 B2 | 8/2006 | Littrup et al. |
| 7,195,616 B2 | 3/2007 | Diller et al. |
| 7,217,939 B2 | 5/2007 | Johansson et al. |
| 7,250,046 B1 | 7/2007 | Fallat |
| 7,311,672 B2 | 12/2007 | Van Bladel et al. |
| 7,367,341 B2 | 5/2008 | Anderson et al. |
| 7,402,140 B2 | 7/2008 | Spero et al. |
| 7,422,586 B2 | 9/2008 | Morris et al. |
| 7,578,819 B2 | 8/2009 | Bleich et al. |
| 7,641,679 B2 | 1/2010 | Joye et al. |
| 7,713,266 B2 | 5/2010 | Elkins et al. |
| 7,850,683 B2 | 12/2010 | Elkins et al. |
| 7,862,558 B2 | 1/2011 | Elkins et al. |
| 7,998,137 B2 | 8/2011 | Elkins et al. |
| 8,298,216 B2 | 10/2012 | Burger et al. |
| 8,409,185 B2 | 4/2013 | Burger et al. |
| 8,715,275 B2 | 5/2014 | Burger et al. |
| 2002/0010460 A1 | 1/2002 | Joye et al. |
| 2002/0013602 A1 | 1/2002 | Huttner |
| 2002/0045434 A1 | 4/2002 | Masoian et al. |
| 2002/0049436 A1 | 4/2002 | Zvuloni et al. |
| 2002/0068929 A1 | 6/2002 | Zvuloni |
| 2002/0120260 A1 | 8/2002 | Morris et al. |
| 2002/0120261 A1 | 8/2002 | Morris et al. |
| 2002/0120263 A1 | 8/2002 | Brown et al. |
| 2002/0128638 A1 | 9/2002 | Chauvet et al. |
| 2002/0156469 A1 | 10/2002 | Yon et al. |
| 2002/0183731 A1 | 12/2002 | Holland et al. |
| 2002/0193778 A1 | 12/2002 | Alchas et al. |
| 2003/0036752 A1 | 2/2003 | Joye et al. |
| 2003/0109912 A1 | 6/2003 | Joye et al. |
| 2003/0130575 A1 | 7/2003 | Desai |
| 2003/0181896 A1 | 9/2003 | Zvuloni et al. |
| 2003/0195436 A1 | 10/2003 | Van Bladel et al. |
| 2003/0220635 A1 | 11/2003 | Knowlton et al. |
| 2003/0220674 A1 | 11/2003 | Anderson et al. |
| 2004/0024391 A1 | 2/2004 | Cytron et al. |
| 2004/0024392 A1 * | 2/2004 | Lewis .................. A61B 18/02 606/22 |
| 2004/0082943 A1 | 4/2004 | Littrup et al. |
| 2004/0092875 A1 | 5/2004 | Kochamba |
| 2004/0122482 A1 | 6/2004 | Tung et al. |
| 2004/0143252 A1 | 7/2004 | Hurst |
| 2004/0162551 A1 | 8/2004 | Brown et al. |
| 2004/0167505 A1 | 8/2004 | Joye et al. |
| 2004/0191229 A1 | 9/2004 | Link et al. |
| 2004/0204705 A1 * | 10/2004 | Lafontaine ............ A61B 18/02 606/21 |
| 2004/0210212 A1 | 10/2004 | Maurice |
| 2004/0215178 A1 | 10/2004 | Maurice |
| 2004/0215294 A1 | 10/2004 | Littrup et al. |

(56) References Cited

U.S. PATENT DOCUMENTS

| | | |
|---|---|---|
| 2004/0215295 A1 | 10/2004 | Littrup et al. |
| 2004/0220497 A1 | 11/2004 | Findlay et al. |
| 2004/0220648 A1 | 11/2004 | Carroll |
| 2004/0225276 A1 | 11/2004 | Burgess |
| 2004/0243116 A1 | 12/2004 | Joye et al. |
| 2004/0267248 A1 | 12/2004 | Duong et al. |
| 2004/0267257 A1 | 12/2004 | Bourne et al. |
| 2005/0004563 A1 | 1/2005 | Racz et al. |
| 2005/0177147 A1 | 8/2005 | Vancelette et al. |
| 2005/0177148 A1 | 8/2005 | van der Walt et al. |
| 2005/0182394 A1 | 8/2005 | Spero et al. |
| 2005/0203505 A1 | 9/2005 | Megerman et al. |
| 2005/0203593 A1 | 9/2005 | Shanks et al. |
| 2005/0209565 A1 | 9/2005 | Yuzhakov et al. |
| 2005/0209587 A1 | 9/2005 | Joye et al. |
| 2005/0224086 A1 | 10/2005 | Nahon |
| 2005/0228288 A1 | 10/2005 | Hurst |
| 2005/0251103 A1 | 11/2005 | Steffen et al. |
| 2005/0261753 A1 | 11/2005 | Littrup et al. |
| 2005/0276759 A1 | 12/2005 | Roser et al. |
| 2005/0281530 A1 | 12/2005 | Rizoiu et al. |
| 2005/0283148 A1 | 12/2005 | Janssen et al. |
| 2006/0009712 A1 | 1/2006 | Van Bladel et al. |
| 2006/0015092 A1 | 1/2006 | Joye et al. |
| 2006/0069385 A1 | 3/2006 | Lafontaine et al. |
| 2006/0079914 A1 | 4/2006 | Modesitt et al. |
| 2006/0084962 A1 | 4/2006 | Joye et al. |
| 2006/0089688 A1 | 4/2006 | Panescu |
| 2006/0111732 A1 | 5/2006 | Gibbens et al. |
| 2006/0129142 A1 | 6/2006 | Reynolds |
| 2006/0142785 A1 | 6/2006 | Modesitt et al. |
| 2006/0173469 A1 | 8/2006 | Klein et al. |
| 2006/0189968 A1 | 8/2006 | Howlett et al. |
| 2006/0190035 A1 | 8/2006 | Hushka et al. |
| 2006/0200117 A1 | 9/2006 | Hermans |
| 2006/0212028 A1 | 9/2006 | Joye et al. |
| 2006/0212048 A1 | 9/2006 | Crainich |
| 2006/0223052 A1 | 10/2006 | MacDonald et al. |
| 2006/0224149 A1 | 10/2006 | Hillely |
| 2006/0258951 A1 | 11/2006 | Bleich et al. |
| 2007/0060921 A1 | 3/2007 | Janssen et al. |
| 2007/0088217 A1 | 4/2007 | Babaev |
| 2007/0129714 A1* | 6/2007 | Elkins .................. A61B 18/02 606/21 |
| 2007/0156125 A1 | 7/2007 | DeLonzor |
| 2007/0161975 A1 | 7/2007 | Goulko |
| 2007/0167943 A1 | 7/2007 | Janssen et al. |
| 2007/0167959 A1 | 7/2007 | Modesitt et al. |
| 2007/0179509 A1 | 8/2007 | Nagata et al. |
| 2007/0198071 A1 | 8/2007 | Ting et al. |
| 2007/0255362 A1 | 11/2007 | Levinson et al. |
| 2007/0270925 A1 | 11/2007 | Levinson |
| 2007/0299432 A1 | 12/2007 | Arless et al. |
| 2008/0051775 A1 | 2/2008 | Evans |
| 2008/0051776 A1 | 2/2008 | Bliweis et al. |
| 2008/0077201 A1 | 3/2008 | Levinson et al. |
| 2008/0077202 A1 | 3/2008 | Levinson |
| 2008/0077211 A1 | 3/2008 | Levinson et al. |
| 2008/0154254 A1 | 6/2008 | Burger et al. |
| 2008/0183164 A1 | 7/2008 | Elkins et al. |
| 2008/0200910 A1 | 8/2008 | Burger et al. |
| 2008/0287839 A1 | 11/2008 | Rosen et al. |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0118722 A1 | 5/2009 | Ebbers et al. |
| 2009/0171203 A1* | 7/2009 | Avital .................. A61B 18/02 600/439 |
| 2009/0171334 A1 | 7/2009 | Elkins et al. |
| 2009/0248001 A1 | 10/2009 | Burger et al. |
| 2009/0264876 A1 | 10/2009 | Roy et al. |
| 2009/0299355 A1* | 12/2009 | Bencini ................ A61B 18/02 606/21 |
| 2009/0299357 A1 | 12/2009 | Zhou |
| 2009/0306639 A1 | 12/2009 | Nevo et al. |
| 2011/0144631 A1 | 6/2011 | Elkins et al. |
| 2012/0065629 A1 | 3/2012 | Elkins et al. |
| 2012/0089211 A1 | 4/2012 | Curtis et al. |
| 2012/0265187 A1 | 10/2012 | Palmer, III et al. |
| 2013/0324990 A1 | 12/2013 | Burger et al. |
| 2014/0249519 A1 | 9/2014 | Burger et al. |

FOREIGN PATENT DOCUMENTS

| | | |
|---|---|---|
| EP | 395307 | 10/1990 |
| EP | 777123 | 6/1997 |
| EP | 955012 | 11/1999 |
| EP | 1074273 | 2/2001 |
| EP | 1377327 | 9/2007 |
| EP | 1862125 | 12/2007 |
| GB | 1360353 | 7/1974 |
| GB | 1402632 | 8/1975 |
| JP | 60013111 | 1/1985 |
| JP | 02092153 | 3/1990 |
| JP | 04357945 | 12/1992 |
| JP | 05038347 | 2/1993 |
| JP | 10014656 | 1/1998 |
| JP | 2001178737 | 7/2001 |
| JP | 2004511274 | 4/2004 |
| JP | 2005080988 | 3/2005 |
| JP | 2006130055 | 5/2006 |
| JP | 2008515469 | 5/2008 |
| RU | 2254060 | 6/2005 |
| WO | 9749344 | 12/1997 |
| WO | 0197702 | 12/2001 |
| WO | 0202026 | 1/2002 |
| WO | 2004039440 | 5/2004 |
| WO | 2004045434 | 6/2004 |
| WO | 2004089460 | 10/2004 |
| WO | 2005000106 | 1/2005 |
| WO | 2005079321 | 9/2005 |
| WO | 2005096979 | 10/2005 |
| WO | 2006012128 | 2/2006 |
| WO | 2006023348 | 3/2006 |
| WO | 2006044727 | 4/2006 |
| WO | 2006062788 | 6/2006 |
| WO | 2006125835 | 11/2006 |
| WO | 2006127467 | 11/2006 |
| WO | 2007025106 | 3/2007 |
| WO | 2007037326 | 4/2007 |
| WO | 2007089603 | 8/2007 |
| WO | 2007129121 | 11/2007 |
| WO | 2007135629 | 11/2007 |
| WO | 2009026471 | 2/2009 |
| WO | 2010075438 | 7/2010 |
| WO | 2010075448 | 7/2010 |
| WO | 2013106859 | 7/2013 |

OTHER PUBLICATIONS

"Cryosurgery probes and accessories catalogue", Metrum CryoFlex, 2009, 25 pages.

Advanced Cosmetic Intervention, "New Technology Targets Motor Nerves", [webpage], retrieved from the Internet: «http://www.acisurgery.com» copyright 2007, 1 page.

Cryopen, LLC, "CyroPen, Llc Launches Revolutionary, State-of-the-Art Medical Device—The Dure of Cryosurgery in a Pend", retrieved from the Internet: «http://cryopen.com/press.htm», Apr. 27, 2007, 3 pages.

Cryopen, LLC, "The future of Cryosurgery at your fingertips", retrieved from the Internet: «http://cryopen.com/» copyright 2006-2008, 2 pages.

Cryosurgical Concepts, Inc., "CryoProbe™—Excellence in Cryosurgery", retrieved from the Internet: «http://www.cryo-surgical.com/», Feb. 8, 2008, 2 pages.

Dasiou-Plankida , "Fat injections for facial rejuvenation: 17 years experience in 1720 patients", Journal of Cosmetic Dermatology, vol. 2, Issue 3-4, Oct. 22, 2004, pp. 119-125.

(56) References Cited

OTHER PUBLICATIONS

Foster et al., "Radiofrequency Ablation of Facial Nerve Branches Controlling Glabellar Frowning", Dermatol Surg, vol. 35, issue 12, Dec. 2009, pp. 1908-1917.

Har-Shai et al., "Effect of skin surface temperature on skin pigmentation during contact and intralesional cryosurgery of hypertrophic scars and Kleoids", Journal of the European Academy of Dermatology and Venereology, vol. 21, Issue 2, Feb. 2007, pp. 191-198.

Magalov et al., "Isothermal volume contours generated in a freezing gel by embedded cryo-needles with applications to cryo-surgery", Cryobiology, vol. 55, Issue 2, Oct. 2007, pp. 127-137.

One Med Group, LLC, "CryoProbeTM", [webpage] retrieved from the internet: <http://www.onemedgroup.com//>, Feb. 4, 2008, 2 pages.

Rewcastle et al., "A model for the time dependent three-dimensional thermal distribution within iceballs surrounding multiple cryoprobes", Medical Physics, vol. 28, Issue 6, Jun. 2001, pp. 1125-1137.

Rutkove, "Effects of temperature on neuromuscular electrophysiology", Muscles and Nerves, vol. 24, Issue 7, Jun. 12, 2001, pp. 867-882.

Utley et al., "Radiofrequency ablation of the nerve to the corrugator muscle for elimination of glabellar furrowing", Archives of Facial Plastic Surgery, vol. 1, No. 1, Jan. 1999, pp. 46-48.

Yang et al., "Apoptosis induced by cryo-injury in human colorectal cancer cells is associated with mitochondrial dysfunction", International Journal of Cancer, vol. 103, Issue 3, Jan. 2003, pp. 360-369.

\* cited by examiner

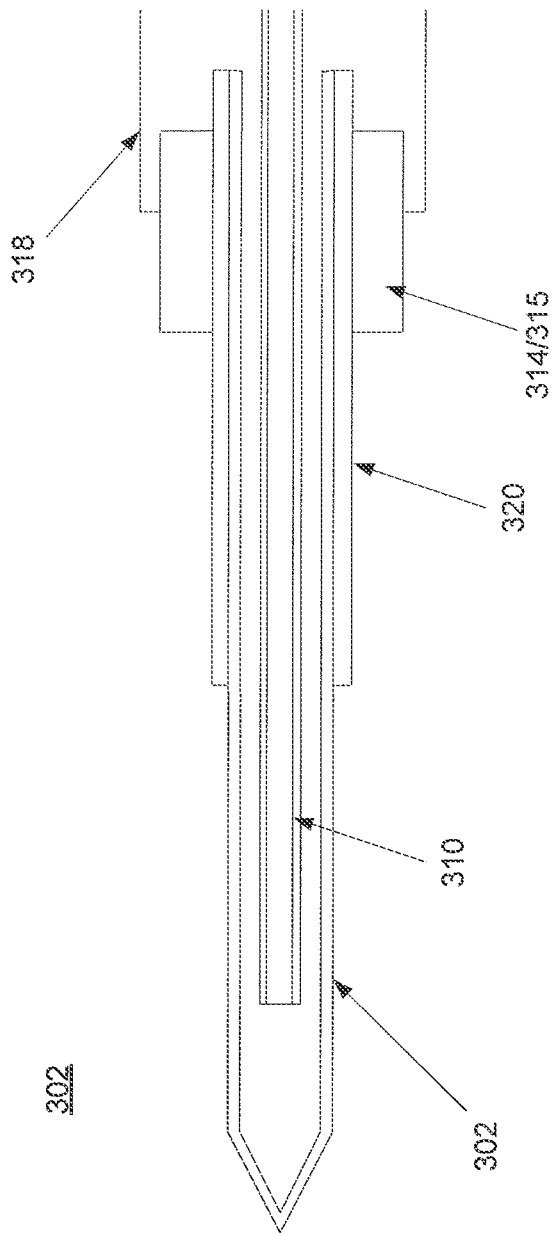

CRYOGENIC NEEDLE WITH FREEZE ZONE REGULATION

CROSS REFERENCE TO RELATED APPLICATION DATA

The present application is a Divisional of U.S. Ser. No. 13/741,360 filed Jan. 14, 2013 (Allowed); which application claims the benefit of U.S. Provisional Appln. No. 61/586,694 filed Jan. 13, 2012; the full disclosures which are incorporated herein by reference in their entirety for all purposes.

BACKGROUND OF THE INVENTION

The present invention is generally directed to medical devices, systems, and methods, particularly for cooling-induced remodeling of tissues. Embodiments of the invention include devices, systems, and methods for applying cryogenic cooling to dermatological tissues so as to selectively remodel one or more target tissues along and/or below an exposed surface of the skin. Embodiments may be employed for a variety of cosmetic conditions, optionally by inhibiting undesirable and/or unsightly effects on the skin (such as lines, wrinkles, or cellulite dimples) or on other surrounding tissue. Other embodiments may find use for a wide range of medical indications. The remodeling of the target tissue may achieve a desired change in its behavior or composition.

The desire to reshape various features of the human body to either correct a deformity or merely to enhance one's appearance is common. This is evidenced by the growing volume of cosmetic surgery procedures that are performed annually.

Many procedures are intended to change the surface appearance of the skin by reducing lines and wrinkles. Some of these procedures involve injecting fillers or stimulating collagen production. More recently, pharmacologically based therapies for wrinkle alleviation and other cosmetic applications have gained in popularity.

Botulinum toxin type A (BOTOX®) is an example of a pharmacologically based therapy used for cosmetic applications. It is typically injected into the facial muscles to block muscle contraction, resulting in temporary enervation or paralysis of the muscle. Once the muscle is disabled, the movement contributing to the formation of the undesirable wrinkle is temporarily eliminated. Another example of pharmaceutical cosmetic treatment is mesotherapy, where a cocktail of homeopathic medication, vitamins, and/or drugs approved for other indications is injected into the skin to deliver healing or corrective treatment to a specific area of the body. Various cocktails are intended to effect body sculpting and cellulite reduction by dissolving adipose tissue, or skin resurfacing via collagen enhancement. Development of non-pharmacologically based cosmetic treatments also continues. For example, endermology is a mechanical based therapy that utilizes vacuum suction to stretch or loosen fibrous connective tissues which are implicated in the dimpled appearance of cellulite.

While BOTOX® and/or mesotherapies may temporarily reduce lines and wrinkles, reduce fat, or provide other cosmetic benefits they are not without their drawbacks, particularly the dangers associated with injection of a known toxic substance into a patient, the potential dangers of injecting unknown and/or untested cocktails, and the like. Additionally, while the effects of endermology are not known to be potentially dangerous, they are brief and only mildly effective.

In light of the above, improved medical devices, systems, and methods utilizing a cryogenic approach to treating the tissue have been proposed, particularly for treatment of wrinkles, fat, cellulite, and other cosmetic defects. These new techniques can provide an alternative visual appearance improvement mechanism which may replace and/or compliment known bioactive and other cosmetic therapies, ideally allowing patients to decrease or eliminate the injection of toxins and harmful cocktails while providing similar or improved cosmetic results. These new techniques are also promising because they may be performed percutaneously using only local or no anesthetic with minimal or no cutting of the skin, no need for suturing or other closure methods, no extensive bandaging, and limited or no bruising or other factors contributing to extended recovery or patient "down time." Additionally, cryogenic treatments are also desirable since they may be used in the treatment of other cosmetic and/or dermatological conditions (and potentially other target tissues), particularly where the treatments may be provided with greater accuracy and control, less collateral tissue injury and/or pain, and greater ease of use.

While these new cryogenic treatments are promising, careful control of temperature along the cryogenic probe is necessary in order to obtain desired results in the target treatment area as well as to avoid unwanted tissue injury in adjacent areas. Once the probe is introduced into a target treatment area, cooling fluid flows through the probe and probe temperature decreases proximally along the length of the probe toward the probe hub. Ideally, temperature at the probe is known during treatment, however, sensing devices cannot typically be placed within small probes, due to size constraints. Therefore, it would be desirable to provide a cryogenic device that helps control needle temperature despite having a sensorless probe.

BRIEF SUMMARY OF THE INVENTION

Embodiments of the invention provide improved medical devices, systems, and methods. Many of the devices and systems described herein will be beneficial for monitoring operational parameters when cryogenically remodeling target tissue.

One embodiment of the invention relates to a method for cryogenically treating tissue. In the method a needle probe having at least one needle with a distal portion and a proximal portion can be provided. The needle probe can be coupled to a coolant supply system regulated by a valve. The at least one needle can be advanced into target tissue. A valve can be regulated to provide the at least one needle probe with coolant to form an cooling zone in the target tissue. Power can be provided to a heater assembly of the needle probe to protect non-target tissue. At least one characteristic of the heater can be monitored while providing power to the heater. Coolant can be metered to the needle probe using the valve based on a correlation of the monitored characteristic of the heater, such that the cooling zone is substantially maintained within an allowable size tolerance.

In one aspect of the method, at least one monitored characteristic can be temperature or other spatial gradient of the heater assembly.

In another aspect of the method, at least one monitored characteristic can be power supplied to the heater assembly.

In another aspect of the method, metering the coolant includes regulating the valve to halt or decrease coolant flowing in the needle probe long enough for the cooling zone to decrease in size within the allowable size tolerance.

In another aspect of the method, metering the coolant includes regulating the valve to provide or increase coolant flowing in the needle probe long enough for the cooling zone to increase in size within the allowable size tolerance.

In another aspect of the method, the allowable size tolerance is determined by performing a tissue pre-characterization routine using the needle probe.

In another aspect of the method, regulating the valve is based on a predetermined treatment algorithm.

In another aspect of the method, the at least one characteristic of the heater includes at least one of a heater power, heat transfer rate, heat flux, temperature change rate, and temperature differential.

Another embodiment of the invention relates to another method for cryogenically treating tissue. In the method, coolant can be regulated to a needle probe using a valve. The needle probe can have at least one needle and a heater thermally coupled to the at least one needle. Power can be provided to the heater based on power demand from the heater. The power supplied to the heater can be monitored. The monitored power can be correlated with at least one of a tissue characteristic and operating parameter.

In one aspect of the method, the valve can be actuated to provide more or less coolant to the needle probe based on at least one of the correlated tissue characteristic and operating parameter.

In another aspect of the method, power demand is based on maintaining the heater at a particular temperature.

In another aspect of the method, the heater includes a thermally conductive element, with the thermally conductive element being thermally coupled to a proximal skin engaging portion of the needle.

In another aspect of the method, temperature of a thermally conductive element coupled to the heater can be monitored.

In another aspect of the method, the at least one needle can include a sensorless needle.

In another aspect of the method, the at least one sensorless needle can be 25 gauge or smaller.

In another aspect of the method, a user indication can be provided based on the correlation.

In another aspect of the method, the user indication relates to a tissue type.

In another aspect of the method, the user indication relates to needle probe status.

In another aspect of the method, regulating cooling includes operating the valve to provide coolant to the needle probe for a predetermined period of time.

In another aspect of the method, the monitored power can be correlated with an operating parameter indicating malfunction of the valve.

In another aspect of the method, a user alert can be provided based on the malfunction of the valve.

In another aspect of the method, the tissue characteristic comprises tissue type or depth of insertion.

In another aspect of the method, the at least one operating parameter comprises at least one of heat transfer rate, heat flux, temperature change rate, and temperature differential.

Another embodiment of the invention relates to a system including a controller. A cooling supply system having a valve can be controlled by the controller. A needle probe can be coupled to the controller and configured to receive coolant from the coolant supply system. The needle probe can have at least one needle and a heater thermally coupled to the at least one needle. The controller can be configured to regulate coolant to the needle probe using the valve, provide power to the heater based on power demand from the heater, monitor power supplied to the heater, and correlate the monitored power with at least one of a tissue characteristic and operating parameter.

In one aspect of the system, the heater can be further configured to actuate the valve to provide more or less coolant to the needle probe based on at least one of the correlated tissue characteristic and operating parameter.

In another aspect of the system, power demand of the heater can be based on maintaining the heater at a particular temperature.

In another aspect of the system, the heater can be thermally coupled to a thermally conductive element, with the thermally conductive element being thermally coupled to a proximal skin engaging portion of the needle.

In another aspect of the system, the controller can be further configured to monitor temperature of a thermally conductive element coupled to the heater.

In another aspect of the system, the at least one cryogenic needle can be included least one cryogenic sensorless needle.

In another aspect of the system, the at least one sensorless needle is 25 gauge or smaller.

In another aspect of the system, the controller can be further configured to provide a user indication based on the correlation. Based on the tissue present, at least one operating parameter may change to affect a particular treatment.

In another aspect of the system, the user indication relates to a tissue type.

In another aspect of the system, the user indication relates to needle probe status.

In another aspect of the system, the user indication relates to placement of the needle probe in tissue In another aspect of the system, the controller can be configured to regulate cooling by operating the valve to provide coolant to the needle probe for a predetermined period of time.

In another aspect of the system, the at least one power characteristic can be correlated to an operating parameter indicating malfunction of the valve.

In another aspect of the system, the controller can be configured to provide a user alert based on the malfunction.

In another aspect of the method, the tissue characteristic comprises tissue type or depth of insertion.

In another aspect of the method, the at least one operating parameter comprises at least one of heat transfer rate, heat flux, temperature change rate, and temperature differential.

BRIEF DESCRIPTION OF THE DRAWINGS

FIGS. 3A-3B illustrate an exemplary embodiment of a clad needle probe, according to an embodiment of the invention.

DETAILED DESCRIPTION OF THE INVENTION

Figure 1A:
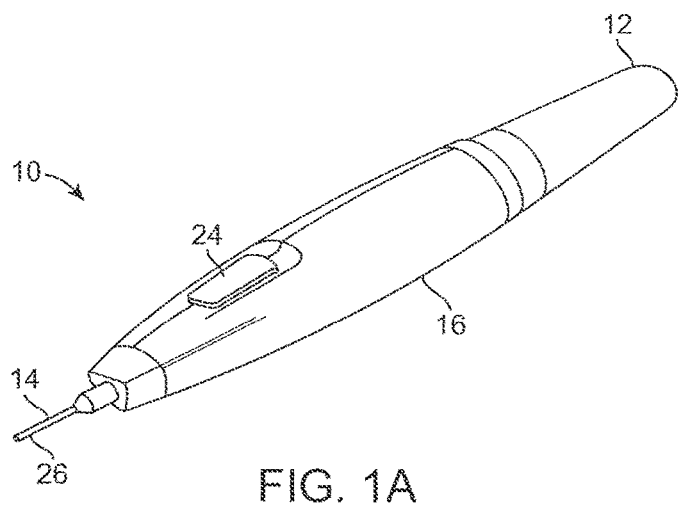
FIG. 1A is a perspective view of a self-contained subdermal cryogenic remodeling probe and system, according to an embodiment of the invention.

The present invention provides improved medical devices, systems, and methods. Embodiments of the invention will facilitate remodeling of target tissues disposed at and below the skin, optionally to treat a cosmetic defect, a lesion, a disease state, and/or so as to alter a shape of the overlying skin surface, while providing protection to portions of non-target tissues, including the skin, which are directly above the target tissues.

Among the most immediate applications of the present invention may be the amelioration of lines and wrinkles, particularly by inhibiting muscular contractions which are associated with these cosmetic defects so as so improve an appearance of the patient. Rather than relying entirely on a pharmacological toxin or the like to disable muscles so as to induce temporary paralysis, many embodiments of the invention will at least in part employ cold to immobilize muscles. Advantageously, nerves, muscles, and associated tissues may be temporarily immobilized using moderately cold temperatures of 10° C. to −5° C. without permanently disabling the tissue structures. Using an approach similar to that employed for identifying structures associated with atrial fibrillation, a needle probe or other treatment device can be used to identify a target tissue structure in a diagnostic mode with these moderate temperatures, and the same probe (or a different probe) can also be used to provide a longer term or permanent treatment, optionally by ablating the target tissue zone and/or inducing apoptosis at temperatures from about −5° C. to about −50° C. In some embodiments, apoptosis may be induced using treatment temperatures from about −1° C. to about −15° C., or from about −1° C. to about −19° C., optionally so as to provide a permanent treatment that limits or avoids inflammation and mobilization of skeletal muscle satellite repair cells. In some embodiments, temporary axonotmesis or neurotmesis degeneration of a motor nerve is desired, which may be induced using treatment temperatures from about −25° C. to about −90° C. Hence, the duration of the treatment efficacy of such subdermal cryogenic treatments may be selected and controlled, with colder temperatures, longer treatment times, and/or larger volumes or selected patterns of target tissue determining the longevity of the treatment. Additional description of cryogenic cooling for treatment of cosmetic and other defects may be found in commonly assigned U.S. Pat. No. 7,713,266 entitled "Subdermal Cryogenic Remodeling of Muscle, Nerves, Connective Tissue, and/or Adipose Tissue (Fat)", U.S. Pat. No. 7,850,683 entitled "Subdermal Cryogenic Remodeling of Muscles, Nerves, Connective Tissue, and/or Adipose Tissue (Fat)", and U.S. patent application Ser. No. 13/325,004, entitled "Method for Reducing Hyperdynamic Facial Wrinkles", the full disclosures of which are each incorporated by reference herein.

In addition to cosmetic treatments of lines, wrinkles, and the like, embodiments of the invention may also find applications for treatments of subdermal adipose tissues, benign, pre-malignant lesions, malignant lesions, acne and a wide range of other dermatological conditions (including dermatological conditions for which cryogenic treatments have been proposed and additional dermatological conditions), and the like. Embodiments of the invention may also find applications for alleviation of pain, including those associated with muscle spasms as disclosed in commonly assigned U.S. Pub. No. 2009/0248001 entitled "Pain Management Using Cryogenic Remodeling" the full disclosure of which is incorporated herein by reference.

Figure 1B:
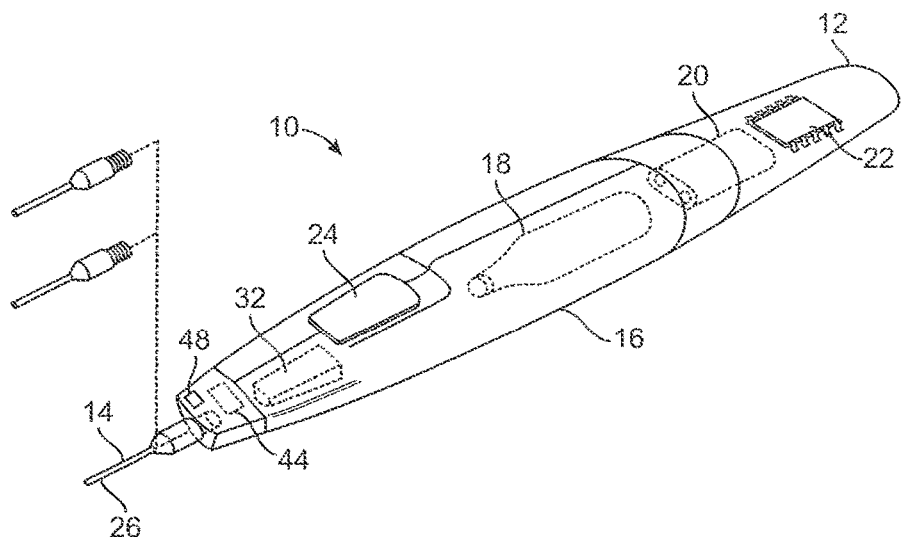
FIG. 1B is a partially transparent perspective view of the self-contained probe of FIG. 1A, showing internal components of the cryogenic remodeling system and schematically illustrating replacement treatment needles for use with the disposable probe.

Referring now to FIGS. 1A and 1B, a system for cryogenic remodeling here comprises a self-contained probe handpiece generally having a proximal end 12 and a distal end 14. A handpiece body or housing 16 has a size and ergonomic shape suitable for being grasped and supported in a surgeon's hand or other system operator. As can be seen most clearly in FIG. 1B, a cryogenic cooling fluid supply 18, a supply valve 32 and electrical power source 20 are found within housing 16, along with a circuit 22 having a processor for controlling cooling applied by self-contained system 10 in response to actuation of an input 24. Alternatively, electrical power can be applied through a cord from a remote power source. Power source 20 also supplies power to heater element 44 in order to heat the proximal region of probe 26 thereby helping to prevent unwanted skin damage, and a temperature sensor 48 adjacent the proximal region of probe 26 helps monitor probe temperature. Additional details on the heater 44 and temperature sensor 48 are described in greater detail below. When actuated, supply valve 32 controls the flow of cryogenic cooling fluid from fluid supply 18. Some embodiments may, at least in part, be manually activated, such as through the use of a manual supply valve and/or the like, so that processors, electrical power supplies, and the like may not be required.

Extending distally from distal end 14 of housing 16 is a tissue-penetrating cryogenic cooling probe 26. Probe 26 is thermally coupled to a cooling fluid path extending from cooling fluid source 18, with the exemplary probe comprising a tubular body receiving at least a portion of the cooling fluid from the cooling fluid source therein. The exemplary probe 26 comprises a 27 g needle having a sharpened distal end that is axially sealed. Probe 26 may have an axial length between distal end 14 of housing 16 and the distal end of the needle of between about 0.5 mm and 5 cm, preferably having a length from about 3 mm to about 10 mm. Such needles may comprise a stainless steel tube with an inner diameter of about 0.006 inches and an outer diameter of about 0.012 inches, while alternative probes may comprise structures having outer diameters (or other lateral cross-sectional dimensions) from about 0.006 inches to about 0.100 inches. Generally, needle probe 26 will comprise a 16 g or smaller size needle, often comprising a 20 g needle or smaller, typically comprising a 25, 26, 27, 28, 29, or 30 g or smaller needle.

In some embodiments, probe 26 may comprise two or more needles arranged in a linear array, such as those disclosed in previously incorporated U.S. Pat. No. 7,850, 683. Another exemplary embodiment of a probe having multiple needle probe configurations allow the cryogenic treatment to be applied to a larger or more specific treatment area. Other needle configurations that facilitate controlling the depth of needle penetration and insulated needle embodiments are disclosed in commonly assigned U.S. Patent Publication No. 2008/0200910 entitled "Replaceable and/or Easily Removable Needle Systems for Dermal and Transdermal Cryogenic Remodeling," the entire content of which is incorporated herein by reference. Multiple needle arrays may also be arrayed in alternative configurations such as a triangular or square array.

Arrays may be designed to treat a particular region of tissue, or to provide a uniform treatment within a particular region, or both. In some embodiments needle 26 is releasably coupled with body 16 so that it may be replaced after use with a sharper needle (as indicated by the dotted line) or with a needle having a different configuration. In exemplary embodiments, the needle may be threaded into the body, it may be press fit into an aperture in the body or it may have a quick disconnect such as a detent mechanism for engaging the needle with the body. A quick disconnect with a check valve is advantageous since it permits decoupling of the needle from the body at any time without excessive coolant discharge. This can be a useful safety feature in the event that the device fails in operation (e.g. valve failure), allowing an operator to disengage the needle and device from a patient's tissue without exposing the patient to coolant as the system depressurizes. This feature is also advantageous because it allows an operator to easily exchange a dull needle with a sharp needle in the middle of a treatment. One of skill in the art will appreciate that other coupling mechanisms may be used.

Addressing some of the components within housing 16, the exemplary cooling fluid supply 18 comprises a canister, sometimes referred to herein as a cartridge, containing a liquid under pressure, with the liquid preferably having a boiling temperature of less than 37° C. When the fluid is thermally coupled to the tissue-penetrating probe 26, and the probe is positioned within the patient so that an outer surface of the probe is adjacent to a target tissue, the heat from the target tissue evaporates at least a portion of the liquid and the enthalpy of vaporization cools the target tissue. A supply valve 32 may be disposed along the cooling fluid flow path between canister 18 and probe 26, or along the cooling fluid path after the probe so as to limit coolant flow thereby regulating the temperature, treatment time, rate of temperature change, or other cooling characteristics. The valve will often be powered electrically via power source 20, per the direction of processor 22, but may at least in part be manually powered. The exemplary power source 20 comprises a rechargeable or single-use battery. Additional details about valve 32 are disclosed below and further disclosure on the power source 20 may be found in commonly assigned Int'l Pub. No. WO 2010/075438 entitled "Integrated Cryosurgical Probe Package with Fluid Reservoir and Limited Electrical Power Source," the entire contents of which is incorporated herein by reference.

The exemplary cooling fluid supply 18 comprises a single-use canister. Advantageously, the canister and cooling fluid therein may be stored and/or used at (or even above) room temperature. The canister may have a frangible seal or may be refillable, with the exemplary canister containing liquid nitrous oxide, $N_2O$. A variety of alternative cooling fluids might also be used, with exemplary cooling fluids including fluorocarbon refrigerants and/or carbon dioxide. The quantity of cooling fluid contained by canister 18 will typically be sufficient to treat at least a significant region of a patient, but will often be less than sufficient to treat two or more patients. An exemplary liquid $N_2O$ canister might contain, for example, a quantity in a range from about 1 gram to about 40 grams of liquid, more preferably from about 1 gram to about 35 grams of liquid, and even more preferably from about 7 grams to about 30 grams of liquid.

Processor 22 will typically comprise a programmable electronic microprocessor embodying machine readable computer code or programming instructions for implementing one or more of the treatment methods described herein. The microprocessor will typically include or be coupled to a memory (such as a non-volatile memory, a flash memory, a read-only memory ("ROM"), a random access memory ("RAM"), or the like) storing the computer code and data to be used thereby, and/or a recording media (including a magnetic recording media such as a hard disk, a floppy disk, or the like; or an optical recording media such as a CD or DVD) may be provided. Suitable interface devices (such as digital-to-analog or analog-to-digital converters, or the like) and input/output devices (such as USB or serial I/O ports, wireless communication cards, graphical display cards, and the like) may also be provided. A wide variety of commercially available or specialized processor structures may be used in different embodiments, and suitable processors may make use of a wide variety of combinations of hardware and/or hardware/software combinations. For example, processor 22 may be integrated on a single processor board and may run a single program or may make use of a plurality of boards running a number of different program modules in a wide variety of alternative distributed data processing or code architectures.

Figure 2:
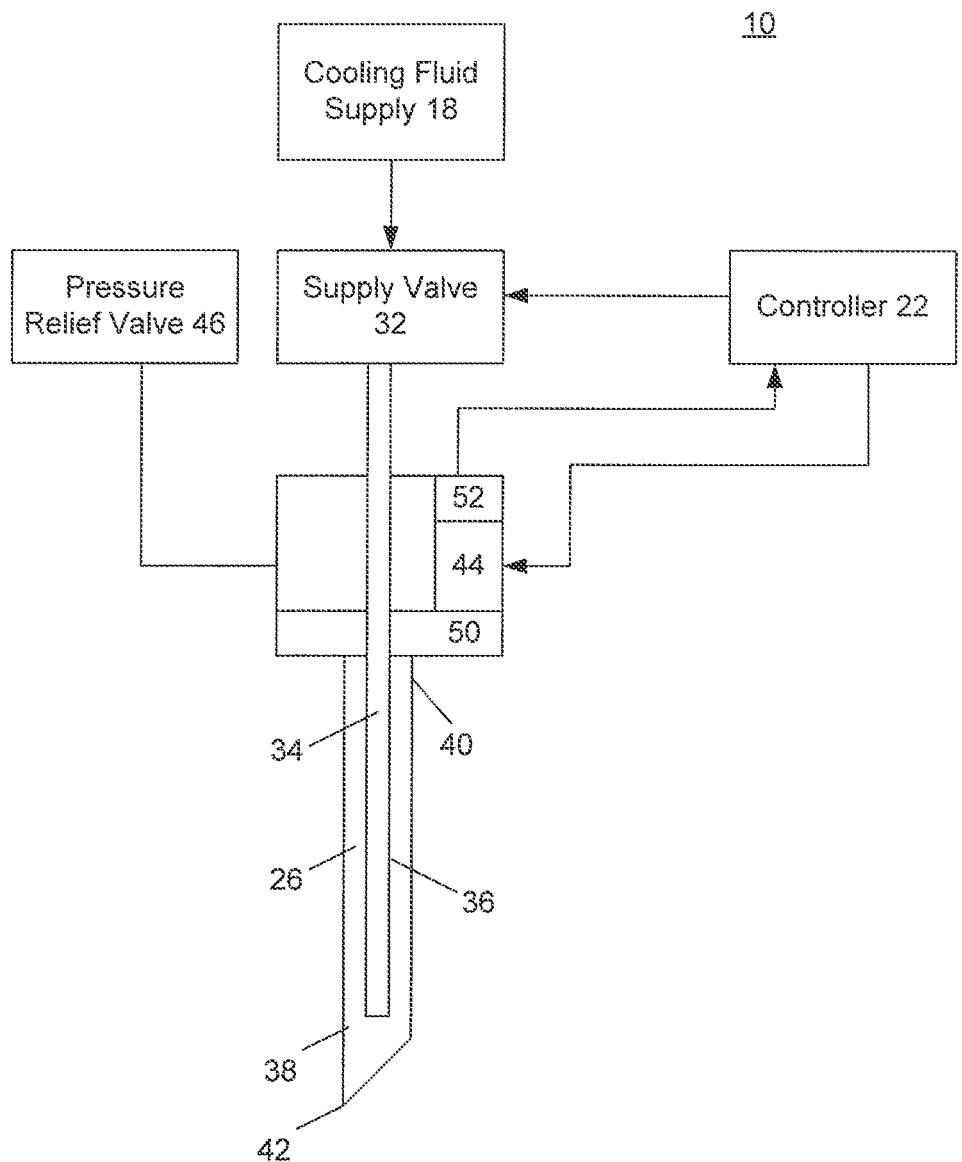
FIG. 2 schematically illustrates components that may be included in the treatment system.

Referring now to FIG. 2, the flow of cryogenic cooling fluid from fluid supply 18 is controlled by a supply valve 32. Supply valve 32 may comprise an electrically actuated solenoid valve, a motor actuated valve or the like operating in response to control signals from controller 22, and/or may comprise a manual valve. Exemplary supply valves may comprise structures suitable for on/off valve operation, and may provide venting of the fluid source and/or the cooling fluid path downstream of the valve when cooling flow is halted so as to limit residual cryogenic fluid vaporization and cooling. Additionally, the valve may be actuated by the controller in order to modulate coolant flow to provide high rates of cooling in some instances where it is desirable to promote necrosis of tissue such as in malignant lesions and the like or slow cooling which promotes ice formation between cells rather than within cells when necrosis is not desired. More complex flow modulating valve structures might also be used in other embodiments. For example, other applicable valve embodiments are disclosed in previously incorporated U.S. Pub. No. 2008/0200910.

Still referring to FIG. 2, an optional heater (not illustrated) may be used to heat cooling fluid supply 18 so that heated cooling fluid flows through valve 32 and through a lumen 34 of a cooling fluid supply tube 36. Supply tube 36 is, at least in part, disposed within a lumen 38 of needle 26, with the supply tube extending distally from a proximal end 40 of the needle toward a distal end 42. The exemplary supply tube 36 comprises a fused silica tubular structure (not illustrated) having a polymer coating and extending in cantilever into the needle lumen 38. Supply tube 36 may have an inner lumen with an effective inner diameter of less than about 200 μm, the inner diameter often being less than about 100 μm, and typically being less than about 40 μm. Exemplary embodiments of supply tube 36 have inner lumens of between about 15 and 50 μm, such as about 30 μm. An outer diameter or size of supply tube 36 will typically be less than about 1000 μm, often being less than about 800 μm, with exemplary embodiments being between about 60 and 150 µm, such as about 90 µm or 105 µm. The tolerance of the inner lumen diameter of supply tubing 36 will preferably be relatively tight, typically being about +/−10 µm or tighter, often being +/−5 µm or tighter, and ideally being +/−3 µm or tighter, as the small diameter supply tube may provide the majority of (or even substantially all of) the metering of the cooling fluid flow into needle 26. Previously incorporated U.S. Patent Publication No. 2008/0200910 discloses additional details on the needle 26 along with various alternative embodiments and principles of operation.

The cooling fluid injected into lumen 38 of needle 26 will typically comprise liquid, though some gas may also be injected. At least some of the liquid vaporizes within needle 26, and the enthalpy of vaporization cools the needle and also the surrounding tissue engaged by the needle. An optional heater 44 (illustrated in FIG. 1B) may be used to heat the proximal region of the needle 26 in order to prevent unwanted skin damage in this area, as discussed in greater detail below. Controlling a pressure of the gas/liquid mixture within needle 26 substantially controls the temperature within lumen 38, and hence the treatment temperature range of the tissue. A relatively simple mechanical pressure relief valve 46 may be used to control the pressure within the lumen of the needle, with the exemplary valve comprising a valve body such as a ball bearing, urged against a valve seat by a biasing spring. An exemplary relief valve is disclosed in U.S. Provisional Patent Application No. 61/116,050 previously incorporated herein by reference. Thus, the relief valve allows better temperature control in the needle, minimizing transient temperatures. Further details on exhaust volume are disclosed in previously incorporated U.S. Pat. Pub. No. 2008/0200910.

The heater 44 may be thermally coupled to a thermally responsive element 50, which is supplied with power by the controller 22 and thermally coupled to a proximal portion of the needle 26. The thermally responsive element 50 can be a block constructed from a material of high thermal conductivity and low heat capacity, such as aluminum. A first temperature sensor 52 (e.g., thermistor, thermocouple) can also be thermally coupled the thermally responsive element 50 and communicatively coupled to the controller 22. A second temperature sensor 53 can also be positioned near the heater 44, for example, such that the first temperature sensor 52 and second temperature sensor 44 are placed in different positions within the thermally responsive element 50. In some embodiments, the second temperature sensor 53 is placed closer to a tissue contacting surface than the first temperature sensor is in order to provide comparative data (e.g., temperature differential) between the sensors. The controller 22 can be configured to receive temperature information of the thermally responsive element 50 via the temperature sensor 52 in order to provide the heater 44 with enough power to maintain the thermally responsive element 50 at a particular temperature.

The controller 22 can be further configured to monitor power draw from the heater 44 in order to characterize tissue type, perform device diagnostics, and/or provide feedback for a tissue treatment algorithm. This can be advantageous over monitoring temperature alone, since power draw from the heater 44 can vary greatly while temperature of the thermally responsive element 50 remains relatively stable. For example, during treatment of target tissue, maintaining the thermally responsive element 50 at 40° C. during a cooling cycle may take 1.0 W initially and is normally expected to climb to 1.5 W after 20 seconds, due to the needle 26 drawing in surrounding heat. An indication that the heater is drawing 2.0 W after 20 seconds to maintain 40° C. can indicate that an aspect of the system 10 is malfunctioning and/or that the needle 26 is incorrectly positioned. Correlations with power draw and correlated device and/or tissue conditions can be determined experimentally to determine acceptable treatment power ranges.

In some embodiments, it may be preferable to limit frozen tissue that is not at the treatment temperature, i.e., to limit the size of a formed cooling zone within tissue. Such cooling zones may be associated with a particular physical reaction, such as the formation of an ice-ball, or with a particular temperature profile or temperature volume gradient required to therapeutically affect the tissue therein. To achieve this, metering coolant flow could maintain a large thermal gradient at its outside edges. This may be particularly advantageous in applications for creating an array of connected cooling zones (i.e. fence) in a treatment zone, as time would be provided for the treatment zone to fully develop within the fenced in portion of the tissue, while the outer boundaries maintained a relatively large thermal gradient due to the repeated application and removal of refrigeration power. This could provide a mechanism within the body of tissue to thermally regulate the treatment zone and could provide increased ability to modulate the treatment zone at a prescribed distance from the surface of the skin. A related treatment algorithm could be predefined, or it could be in response to feedback from the tissue.

Such feedback could be temperature measurements from the needle 26, or the temperature of the surface of the skin could be measured. However, in many cases monitoring temperature at the needle 26 is impractical due to size constraints. To overcome this, operating performance of the sensorless needle 26 can be interpolated by measuring characteristics of thermally coupled elements, such as the thermally responsive element 50.

One such measured characteristic could be the power required to heat the thermally responsive element 50, therefore the medium which the thermally responsive element 50, or the thermally coupled needle 26, is coupled to. For example, very little power would be required to warm and maintain the temperature of the thermally conductive element 50 in air. Various materials could be characterized. For example, the thermally responsive element 50 could be used to determine whether the thermally responsive element 50, or the thermally coupled needle 26, has sufficient contact with skin due to the thermal load of the skin. This would be useful for ensuring that the needle 26 was correctly placed prior to treatment. This could be done without flowing coolant to the needle 26, or alternatively, by metering very little coolant to the needle 26, i.e., less than what is required to treat tissue.

Once the treatment has started, there may be more or less residual refrigerant that affected the thermally conductive element 50 depending upon how much thermal load was applied to the needle 26. This could be used to characterize the tissue(s) the probes was placed into. For example, there would be relatively more heat drawn from the thermally conductive element 50 in insulative tissue such as adipose tissue. Since thermal load on the distal end of the needle 26 would be affected by the development of an cooling zone around the needle 26, the thermally conductive element 50 could be used to determine the state of the needle 26 as ice forms.

Power feedback could provide feedback to regulate the delivery of refrigerant based upon the tissue, formation of ice, contact with the skin, or other useful information. The feedback could be used to control the treatment zone to the desired configuration. In addition, the feedback could be used to diagnose a treatment failure. For instance if the probe had three needles delivering refrigerant, but only two were working, the thermally conductive element could detect the failure and inform the user.

Temperature feedback could also used in conjunction with power feedback. Temperature sensing could occur on the needle 26 if possible, on the thermally conductive element 50, and/or remote to the thermally conductive element. For example, the thermally conductive element 50 could reside on a detachable cooling probe and be thermally coupled to a handpiece, with feedback and control circuits located within the handpiece (e.g., housing 16). This could be advantageous to provide a low cost detachable cooling probe and for system reliability, since the probe could be coupled to a controller in the reusable handpiece. Thus, practically offering higher capability due to the ability to afford more precise controls.

The thermally conductive element 50 could be thermally coupled to the needle 26 at a proximal tissue interface. When refrigerant was delivered, excess refrigerant would return through the needle. The excess refrigerant could be in the form of cool gas or liquid that had not yet converted to gas through the latent heat of vaporization. The excess refrigerant could change dependent upon the tissue(s) the probe was in, variations in tissue temperature, presence of local heat sources (arteries and veins), and metabolic effects. The excess refrigerant could also be affected by the effect of the treatment over time. In particular, changes in thermal loading as a function of the cooling of adjacent tissue and the formation of ice. The thermally conductive element could be tailored to deliver comparable, or more heat than the available refrigeration power. However, the transfer of heat into the tissue would be constrained by the material and dimensions of the needle. For example, a relatively long needle might receive enough heat from the adjacent tissue along its length to prevent the freeze zone from extending more proximally than desired. Alternatively the ability to transfer more heat into the tissue could be achieved by providing improved thermal coupling from the thermally conductive element 50 into the tissue. This could be achieved by increasing the diameter and or wall thickness of the needle, or through the addition of thermally conductive cladding to the proximal portion of the needle. This coupling could also be optimized to extend the length of the protection desired. For instance, the cladding or portion of increased wall thickness and diameter could extend through the dermis and subdermal fat layer, then end. Further the cooling of the tip and the heating of more proximal tissue could be uncoupled. This could be achieved by applying an insulative material between the cladding and the underlying needle. Therefore, the heat through the protected portion of tissue could be controlled independent of the refrigeration of the tip. This would be advantageous in that the heat added would not compromise the refrigerant delivered to the tip and the refrigerant would not comprise the heat added to the tissue.

Additional methods of monitoring cooling and maintaining an unfrozen portion of the needle include the addition of a heating element and/or monitoring element into the needle itself. This could consist of a small thermistor or thermocouple, and a wire that could provide resistive heat. Other power sources could also be applied such as infrared light, radiofrequency heat, and ultrasound. These systems could also be applied together dependent upon the control of the treatment zone desired.

Alternative methods to inhibit excessively low transient temperatures at the beginning of a refrigeration cycle might be employed instead of or together with the limiting of the exhaust volume. For example, the supply valve might be cycled on and off, typically by controller 22, with a timing sequence that would limit the cooling fluid flowing so that only vaporized gas reached the needle lumen (or a sufficiently limited amount of liquid to avoid excessive dropping of the needle lumen temperature). This cycling might be ended once the exhaust volume pressure was sufficient so that the refrigeration temperature would be within desired limits during steady state flow. Analytical models that may be used to estimate cooling flows are described in greater detail in previously incorporated U.S. Patent Pub. No. 2008/0154,254.

Referring now to FIG. 2, the flow of cryogenic cooling fluid from fluid supply 18 is controlled by a supply valve 32. Supply valve 32 may comprise an electrically actuated solenoid valve, a motor actuated valve or the like operating in response to control signals from controller 22, and/or may comprise a manual valve. Exemplary supply valves may comprise structures suitable for on/off valve operation, and may provide venting of the fluid source and/or the cooling fluid path downstream of the valve when cooling flow is halted so as to limit residual cryogenic fluid vaporization and cooling. Additionally, the valve may be actuated by the controller in order to modulate coolant flow to provide high rates of cooling in some instances where it is desirable to promote necrosis of tissue such as in malignant lesions and the like or slow cooling which promotes ice formation between cells rather than within cells when necrosis is not desired. More complex flow modulating valve structures might also be used in other embodiments. For example, other applicable valve embodiments are disclosed in previously incorporated U.S. Pub. No. 2008/0200910.

Still referring to FIG. 2, an optional cooling supply heater (not illustrated) may be used to heat cooling fluid supply 18 so that heated cooling fluid flows through valve 32 and through a lumen 34 of a cooling fluid supply tube 36. In some embodiments safety mechanism can be included so that the cooling supply is not overheated. Examples of such embodiments are disclosed in commonly assigned Int'l. Pub. No. WO 2010075438, the entirety of which is incorporated by reference herein.

Supply tube 36 is, at least in part, disposed within a lumen 38 of needle 26, with the supply tube extending distally from a proximal end 40 of the needle toward a distal end 42. The exemplary supply tube 36 comprises a fused silica tubular structure (not illustrated) having a polymer coating and extending in cantilever into the needle lumen 38. Supply tube 36 may have an inner lumen with an effective inner diameter of less than about 200 µm, the inner diameter often being less than about 100 µm, and typically being less than about 40 µm. Exemplary embodiments of supply tube 36 have inner lumens of between about 15 and 50 µm, such as about 30 µm. An outer diameter or size of supply tube 36 will typically be less than about 1000 µm, often being less than about 800 µm, with exemplary embodiments being between about 60 and 150 µm, such as about 90 µm or 105 µm. The tolerance of the inner lumen diameter of supply tubing 36 will preferably be relatively tight, typically being about +/−10 µm or tighter, often being +/−5 µm or tighter, and ideally being +/−3 µm or tighter, as the small diameter supply tube may provide the majority of (or even substantially all of) the metering of the cooling fluid flow into needle 26. Additional details on various aspects of needle 26 along with alternative embodiments and principles of operation are disclosed in greater detail in U.S. Patent Publication No. 2008/0154254 entitled "Dermal and Transdermal Cryogenic Microprobe Systems and Methods," the entire contents of which are incorporated herein by reference. U.S. Patent Pub. No. 2008/0200910, previously incorporated herein by reference, also discloses additional details on the needle 26 along with various alternative embodiments and principles of operation.

The cooling fluid injected into lumen 38 of needle 26 will typically comprise liquid, though some gas may also be injected. At least some of the liquid vaporizes within needle 26, and the enthalpy of vaporization cools the needle and also the surrounding tissue engaged by the needle. An optional heater 44 (illustrated in FIG. 1B) may be used to heat the proximal region of the needle in order to prevent unwanted skin damage in this area, as discussed in greater detail below. Controlling a pressure of the gas/liquid mixture within needle 26 substantially controls the temperature within lumen 38, and hence the treatment temperature range of the tissue. A relatively simple mechanical pressure relief valve 46 may be used to control the pressure within the lumen of the needle, with the exemplary valve comprising a valve body such as a ball bearing, urged against a valve seat by a biasing spring. Thus, the relief valve allows better temperature control in the needle, minimizing transient temperatures. Further details on exhaust volume are disclosed in U.S. Patent Publication No. 2008/0200910, previously incorporated herein by reference.

Alternative methods to inhibit excessively low transient temperatures at the beginning of a refrigeration cycle might be employed instead of or together with the limiting of the exhaust volume. For example, the supply valve might be cycled on and off, typically by controller 22, with a timing sequence that would limit the cooling fluid flowing so that only vaporized gas reached the needle lumen (or a sufficiently limited amount of liquid to avoid excessive dropping of the needle lumen temperature). This cycling might be ended once the exhaust volume pressure was sufficient so that the refrigeration temperature would be within desired limits during steady state flow. Analytical models that may be used to estimate cooling flows are described in greater detail in U.S. Pub. No. 2008/0154254, previously incorporated herein by reference.

Figure 3A:
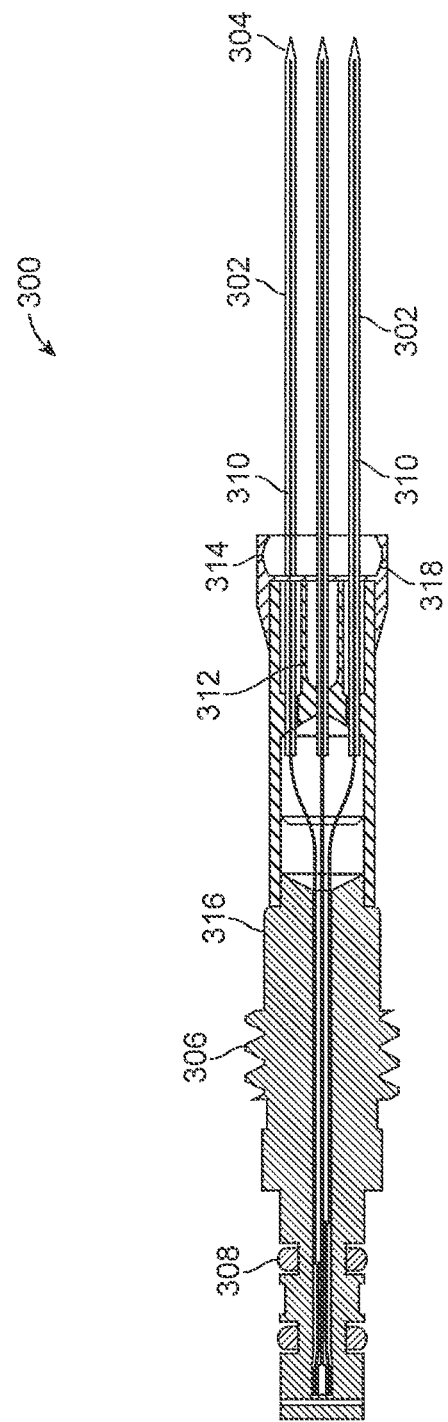

In the exemplary embodiment of FIG. 3A, resistive heater element 314 is disposed near the needle hub 318 and near a proximal region of needle shaft 302. The resistance of the heater element is preferably 1Ω to 1K Ω, and more preferably from 5Ω to 50Ω. Additionally, a temperature sensor 312 such as a thermistor or thermocouple is also disposed in the same vicinity. Thus, during a treatment as the needles cool down, the heater 314 may be turned on in order to heat the hub 318 and proximal region of needle shaft 302, thereby preventing this portion of the device from cooling down as much as the remainder of the needle shaft 302. The temperature sensor 312 may provide feedback to controller 22 and a feedback loop can be used to control the heater 314. The cooling power of the nitrous oxide will eventually overcome the effects of the heater, therefore the microprocessor may also be programmed with a warning light and/or an automatic shutoff time to stop the cooling treatment before skin damage occurs. An added benefit of using such a heater element is the fact that the heat helps to moderate the flow of cooling fluid into the needle shaft 302 helping to provide more uniform coolant mass flow to the needles shaft 302 with more uniform cooling resulting.

The embodiment of FIG. 3A illustrates a heater fixed to the probe hub. In other embodiments, the heater may float, thereby ensuring proper skin contact and proper heat transfer to the skin. Examples of floating heaters are disclosed in commonly assigned Int'l Pub. No. WO 2010/075448 entitled "Skin Protection for Subdermal Cryogenic Remodelling for Cosmetic and Other Treatments", the entirety of which is incorporated by reference herein.

In this exemplary embodiment, three needles are illustrated. One of skill in the art will appreciate that a single needle may be used, as well as two, four, five, six, or more needles may be used. When a plurality of needles are used, they may be arranged in any number of patterns. For example, a single linear array may be used, or a two dimensional or three dimensional array may be used. Examples of two dimensional arrays include any number of rows and columns of needles (e.g. a rectangular array, a square array, elliptical, circular, triangular, etc.), and examples of three dimensional arrays include those where the needle tips are at different distances from the probe hub, such as in an inverted pyramid shape.

FIG. 3B illustrates a cross-section of the needle shaft 302 of needle probe 300. The needle shaft can be conductively coupled (e.g., welded, conductively bonded, press fit) to a conductive heater 314 to enable heat transfer therebetween. The needle shaft 302 is generally a small (e.g., 20-30 gauge) closed tip hollow needle, which can be between about 0.2 mm and 5 cm, preferably having a length from about 0.3 cm to about 0.6 cm. The conductive heater element 314 can be housed within a conductive block 315 of high thermally conductive material, such as aluminum and include an electrically insulated coating, such as Type III anodized coating to electrically insulate it without diminishing its heat transfer properties. The conductive block 315 can be heated by a resister or other heating element (e.g. cartridge heater, nichrome wire, etc.) bonded thereto with a heat conductive adhesive, such as epoxy. A thermistor can be coupled to the conductive block 315 with heat conductive epoxy allows temperature monitoring. Other temperature sensors may also be used, such as a thermocouple.

A cladding 320 of conductive material is directly conductively coupled to the proximal portion of the shaft of needle shaft 302, which can be stainless steel. In some embodiments, the cladding 320 is a layer of gold, or alloys thereof, coated on the exterior of the proximal portion of the needle shaft 302. In some embodiments, the exposed length of cladding 320 on the proximal portion of the needle is 2 mm. In some embodiments, the cladding 320 be of a thickness such that the clad portion has a diameter ranging from 0.017-0.020 in., and in some embodiments 0.0182 in. Accordingly, the cladding 320 can be conductively coupled to the material of the needle 302, which can be less conductive, than the cladding 320.

In some embodiments, the cladding 320 can include sub-coatings (e.g., nickel) that promote adhesion of an outer coating that would otherwise not bond well to the needle shaft 302. Other highly conductive materials can be used as well, such as copper, silver, aluminum, and alloys thereof. In some embodiments, a protective polymer or metal coating can cover the cladding to promote biocompatibility of an otherwise non-biocompatible but highly conductive cladding material. Such a biocompatible coating however, would be applied to not disrupt conductivity between the conductive block 315. In some embodiments, an insulating layer, such as a ceramic material, is coated over the cladding 320, which remains conductively coupled to the needle shaft 302.

In use, the cladding 320 can transfer heat to the proximal portion of the needle 302 to prevent directly surrounding tissue from dropping to cryogenic temperatures. Protection can be derived from heating the non-targeting tissue during a cooling procedure, and in some embodiments before the procedure as well. The mechanism of protection may be providing latent heat to pressurized cryogenic cooling fluid passing within the proximal portion of the needle to affect complete vaporization of the fluid. Thus, the non-target tissue in contact with the proximal portion of the needle shaft 302 does not need to supply latent heat, as opposed to target tissue in contact with the distal region of the needle shaft 302. To help further this effect, in some embodiments the cladding 320 is coating within the interior of the distal portion of the needle, with or without an exterior cladding. To additionally help further this effect, in some embodiments, the distal portion of the needle can be thermally isolated from the proximal portion by a junction, such as a ceramic junction. While in some further embodiments, the entirety of the proximal portion is constructed from a more conductive material than the distal portion.

In use, it has been determined experimentally that the cladding 320 can help limit formation of an cooling zone to the distal portion of the needle shaft 302, which tends to demarcate at a distal end of the cladding 320. This effect is shown depicted in FIG. 3C where non-target tissue, directly above target tissue, including skin and at least a portion of subcutaneous tissue are not made part of the ice-ball. Rather, cooling zones are formed only about the distal portions of the needles—in this case to target a temporal nerve branch. Thus, while non-target tissue in direct contact with proximal needle shafts remain protected from effects of cryogenic temperatures. Such effects can include discoloration and blistering of the skin.

Figure 4:
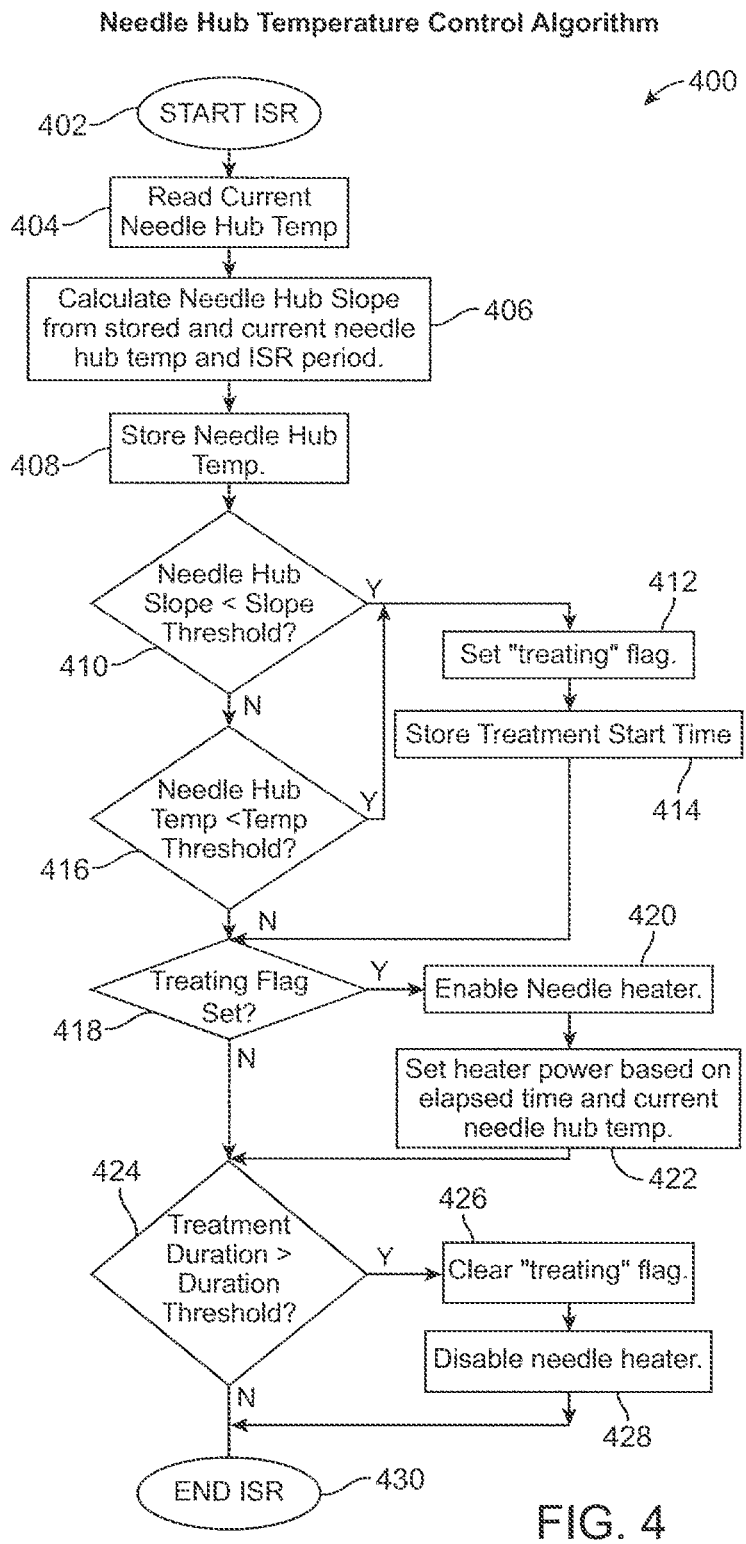
FIG. 4 is a flow chart illustrating an exemplary algorithm for heating the needle probe of FIG. 3A, according to an embodiment of the invention.

An exemplary algorithm 400 for controlling the heater element 314, and thus for transferring heat to the cladding 320, is illustrated in FIG. 4. In FIG. 4, the start of the interrupt service routine (ISR) 402 begins with reading the current needle hub temperature 404 using a temperature sensor such as a thermistor or thermocouple disposed near the needle hub. The time of the measurement is also recorded. This data is fed back to controller 22 where the slope of a line connecting two points is calculated. The first point in the line is defined by the current needle hub temperature and time of its measurement and the second point consists of a previous needle hub temperature measurement and its time of measurement. Once the slope of the needle hub temperature curve has been calculated 406, it is also stored 408 along with the time and temperature data. The needle hub temperature slope is then compared with a slope threshold value 410. If the needle hub temperature slope is less than the threshold value then a treating flag is activated 412 and the treatment start time is noted and stored 414. If the needle hub slope is greater than or equal to the slope threshold value 410, an optional secondary check 416 may be used to verify that cooling has not been initiated. In step 416, absolute needle hub temperature is compared to a temperature threshold. If the hub temperature is less than the temperature threshold, then the treating flag is activated 412 and the treatment start time is recorded 414 as previously described. As an alternative, the shape of the slope could be compared to a norm, and an error flag could be activated for an out of norm condition. Such a condition could indicate the system was not heating or cooling sufficiently. The error flag could trigger an automatic stop to the treatment with an error indicator light. Identifying the potential error condition and possibly stopping the treatment, may prevent damage to the proximal tissue in the form of too much heat, or too much cooling to the tissue. The algorithm preferably uses the slope comparison as the trigger to activate the treatment flag because it is more sensitive to cooling conditions when the cryogenic device is being used rather than simply measuring absolute temperature. For example, a needle probe exposed to a cold environment would gradually cool the needle down and this could trigger the heater to turn on even though no cryogenic cooling treatment was being conducted. The slope more accurately captures rapid decreases in needle temperature as are typically seen during cryogenic treatments.

When the treatment flag is activated 418 the needle heater is enabled 420 and heater power may be adjusted based on the elapsed treatment time and current needle hub temperature 422. Thus, if more heat is required, power is increased and if less heat is required, power is decreased. Whether the treatment flag is activated or not, as an additional safety mechanism, treatment duration may be used to control the heater element 424. As mentioned above, eventually, cryogenic cooling of the needle will overcome the effects of the heater element. In that case, it would be desirable to discontinue the cooling treatment so that the proximal region of the probe does not become too cold and cause skin damage. Therefore, treatment duration is compared to a duration threshold value in step 424. If treatment duration exceeds the duration threshold then the treatment flag is cleared or deactivated 426 and the needle heater is deactivated 428. If the duration has not exceeded the duration threshold 424 then the interrupt service routine ends 430. The algorithm then begins again from the start step 402. This process continues as long as the cryogenic device is turned on.

Preferred ranges for the slope threshold value may range from about −5° C. per second to about −90° C. per second and more preferably range from about −30° C. per second to about −57° C. per second. Preferred ranges for the temperature threshold value may range from about 15° C. to about 0° C., and more preferably may range from about 0° C. to about 10° C. Treatment duration threshold may range from about 15 seconds to about 75 seconds and more preferably may range from about 15 seconds to about 60 seconds.

It should be appreciated that the specific steps illustrated in FIG. 4 provide a particular method of heating a cryogenic probe, according to an embodiment of the present invention. Other sequences of steps may also be performed according to alternative embodiments. For example, alternative embodiments of the present invention may perform the steps outlined above in a different order. Moreover, the individual steps illustrated in FIG. 4 may include multiple sub-steps that may be performed in various sequences as appropriate to the individual step. Furthermore, additional steps may be added or removed depending on the particular applications. One of ordinary skill in the art would recognize many variations, modifications, and alternatives.

Figure 5:
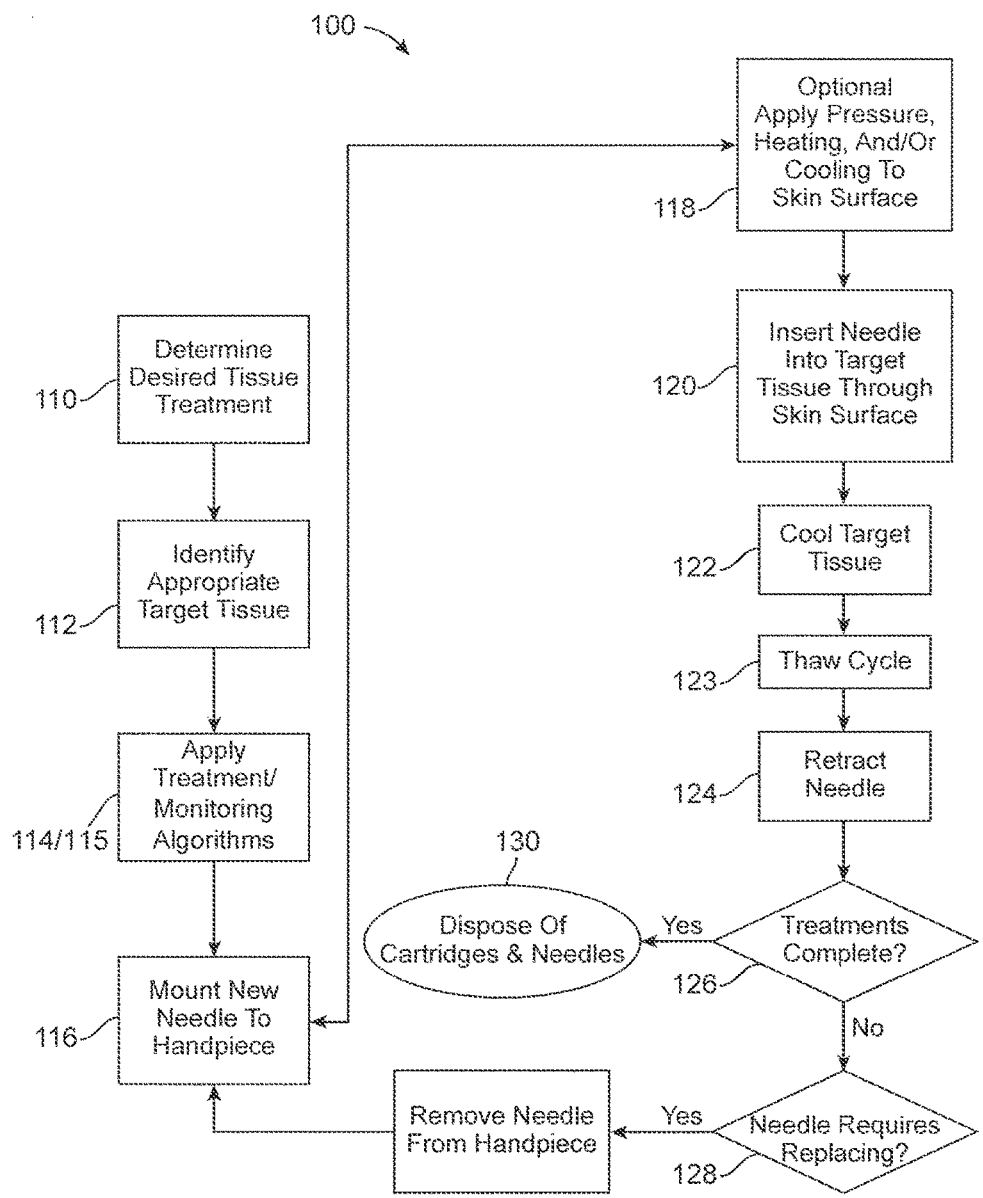
FIG. 5 is a flow chart schematically illustrating a method for treatment using the disposable cryogenic probe and system of FIGS. 1A and 1B, according to an embodiment of the invention.

The heating algorithm may be combined with a method for treating a patient. Referring now to FIG. 5, a method 100 facilitates treating a patient using a cryogenic cooling system having a reusable or disposable handpiece either of which that can be self-contained or externally powered with replaceable needles such as those of FIG. 1B and a limited capacity battery or metered electrical supply. Method 100 generally begins with a determination 110 of the desired tissue therapy and results, such as the alleviation of specific cosmetic wrinkles of the face, the inhibition of pain from a particular site, the alleviation of unsightly skin lesions or cosmetic defects from a region of the face, or the like. Appropriate target tissues for treatment are identified 112 (such as the subdermal muscles that induce the wrinkles, a tissue that transmits the pain signal, or the lesion-inducing infected tissues), allowing a target treatment depth, target treatment temperature profile, or the like to be determined.

Step 112 may include performing a tissue characterization and/or device diagnostic algorithm, based on power draw of system 10, for example.

The application of the treatment algorithm 114 may include the control of multiple parameters such as temperature, time, cycling, pulsing, and ramp rates for cooling or thawing of treatment areas. In parallel with the treatment algorithm 114, one or more power monitoring algorithms 115 can be implemented. An appropriate needle assembly can then be mounted 116 to the handpiece, with the needle assembly optionally having a needle length, skin surface cooling chamber, needle array, and/or other components suitable for treatment of the target tissues. Simpler systems may include only a single needle type, and/or a first needle assembly mounted to the handpiece.

Pressure, heating, cooling, or combinations thereof may be applied 118 to the skin surface adjacent the needle insertion site before, during, and/or after insertion 120 and cryogenic cooling 122 of the needle and associated target tissue. Non-target tissue directly above the target tissue can be protected by directly conducting energy in the form of heat to the cladding on a proximal portion of the needle shaft during cooling. Upon completion of the cryogenic cooling cycle the needles will need additional "thaw" time 123 to thaw from the internally created cooling zone to allow for safe removal of the probe without physical disruption of the target tissues, which may include, but not be limited to nerves, muscles, blood vessels, or connective tissues. This thaw time can either be timed with the refrigerant valve shut-off for as short a time as possible, preferably under 15 seconds, more preferably under 5 seconds, manually or programmed into the controller to automatically shut-off the valve and then pause for a chosen time interval until there is an audible or visual notification of treatment completion.

Heating of the needle may be used to prevent unwanted skin damage using the apparatus and methods previously described. The needle can then be retracted 124 from the target tissue. If the treatment is not complete 126 and the needle is not yet dull 128, pressure and/or cooling can be applied to the next needle insertion location site 118, and the additional target tissue treated. However, as small gauge needles may dull after being inserted only a few times into the skin, any needles that are dulled (or otherwise determined to be sufficiently used to warrant replacement, regardless of whether it is after a single insertion, 5 insertions, or the like) during the treatment may be replaced with a new needle 116 before the next application of pressure/cooling 118, needle insertion 120, and/or the like. Once the target tissues have been completely treated, or once the cooling supply canister included in the self-contained handpiece is depleted, the used canister and/or needles can be disposed of 130. The handpiece may optionally be discarded.

Figure 6A:
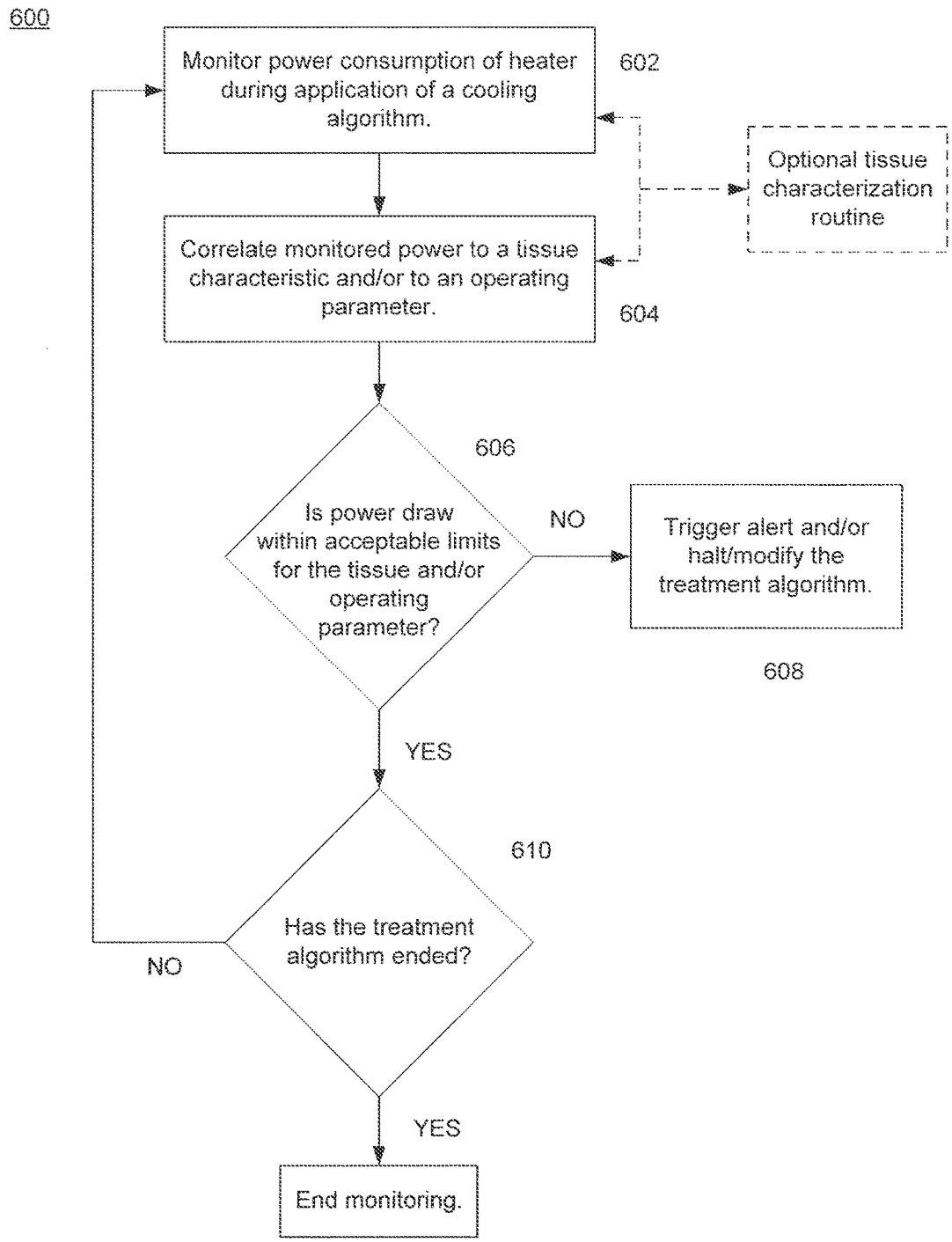
FIG. 6A is a flow chart schematically illustrating a method for treatment using the disposable cryogenic probe and system of FIGS. 1A and 1B, according to an embodiment of the invention.

As discussed with reference to FIG. 5, a power monitoring algorithm 115 can be applied prior to, during, after, and in some cases in lieu of, the treatment algorithm 114, such as the one shown in FIG. 4. One example of a power monitoring algorithm 600 is shown in FIG. 6A, which illustrates a method for monitoring power demand from a heater when cooling fluid is passed through at least one needle. The power monitoring algorithm 600 can be performed during an actual treatment of tissue. At operation 602, the controller (e.g., controller 22) monitors power consumption of a heater (e.g., heater 44), which is thermally coupled to a needle (e.g., needle 26), directly or via a thermally responsive element (e.g., element 50). Monitoring can take place during a tissue treatment procedure, for example, as discussed with reference to FIG. 5, performed in parallel to a treatment algorithm. Alternatively, power monitoring can take place during a diagnostic routine.

At operation 604, the controller correlates a sampled power measurement with an acceptable power range corresponding to a tissue characteristic and/or operating parameter. This measurement may further be correlated according to the time of measurement and temperature of the thermally responsive element 50. For example, during treatment of target tissue, maintaining the thermally responsive element 50 at 40° C. during a cooling cycle may be expected to require 1.0 W initially and is expected to climb to 1.5 W after 20 seconds, due to the needle 26 drawing in surrounding heat. An indication that the heater is drawing 2.0 W after 20 seconds to maintain 40° C. can indicate that an aspect of the system 10 is malfunctioning and/or that the needle 26 is incorrectly positioned within target tissue or primarily positioned in non-target tissue. Correlations with power draw and correlated device and/or tissue conditions can be determined experimentally to determine acceptable power ranges.

At operation 606, the controller determines whether the power measurement is correlated within acceptable limits of an expected power draw, or to a power draw indicating a tissue or device problem. Based on this, a status indication can be provided to the user. If the correlation is unacceptable, then the controller may in operation 608 initiate an alarm to the user and/or halt or modify the treatment algorithm. In some cases, the error is minor, for example, the controller may signal a user indication to modify operator technique, e.g., apply greater or lesser pressure to the skin, or that the needle probe is not fully inserted or that a tissue tent is present. In other cases, the error can indicate a major valve malfunction, and signal an alert to abort the process and/or cause a secondary or purge valve to operate. If the correlation is acceptable, then in operation 610 it is determined whether the treatment algorithm is still in process, which will cause the power monitoring algorithm to end or continue to loop. Alternatively, the power monitoring algorithm 600 can simply loop until interrupted by the controller, for example, when treatment algorithm has ended or by some other trigger.

In some embodiments, the power monitoring algorithm 600 can be performed exclusively for tissue characterization purposes, e.g., to determine proper operating parameters for a later treatment, by only looping between operations 602 and 604 for a predetermined amount of time to collect data. Data can be collected and correlated by the controller to a particular tissue type and further correlated to optimal treatment parameters. For example, the characterized tissue may have a greater or lesser average amount of adjacent adipose tissue, which could require longer or shorter treatment times. This process could be performed, for example, by inserting the needle into the target tissue and providing only enough coolant to characterize the tissue, rather than remodel.

Figure 6B:
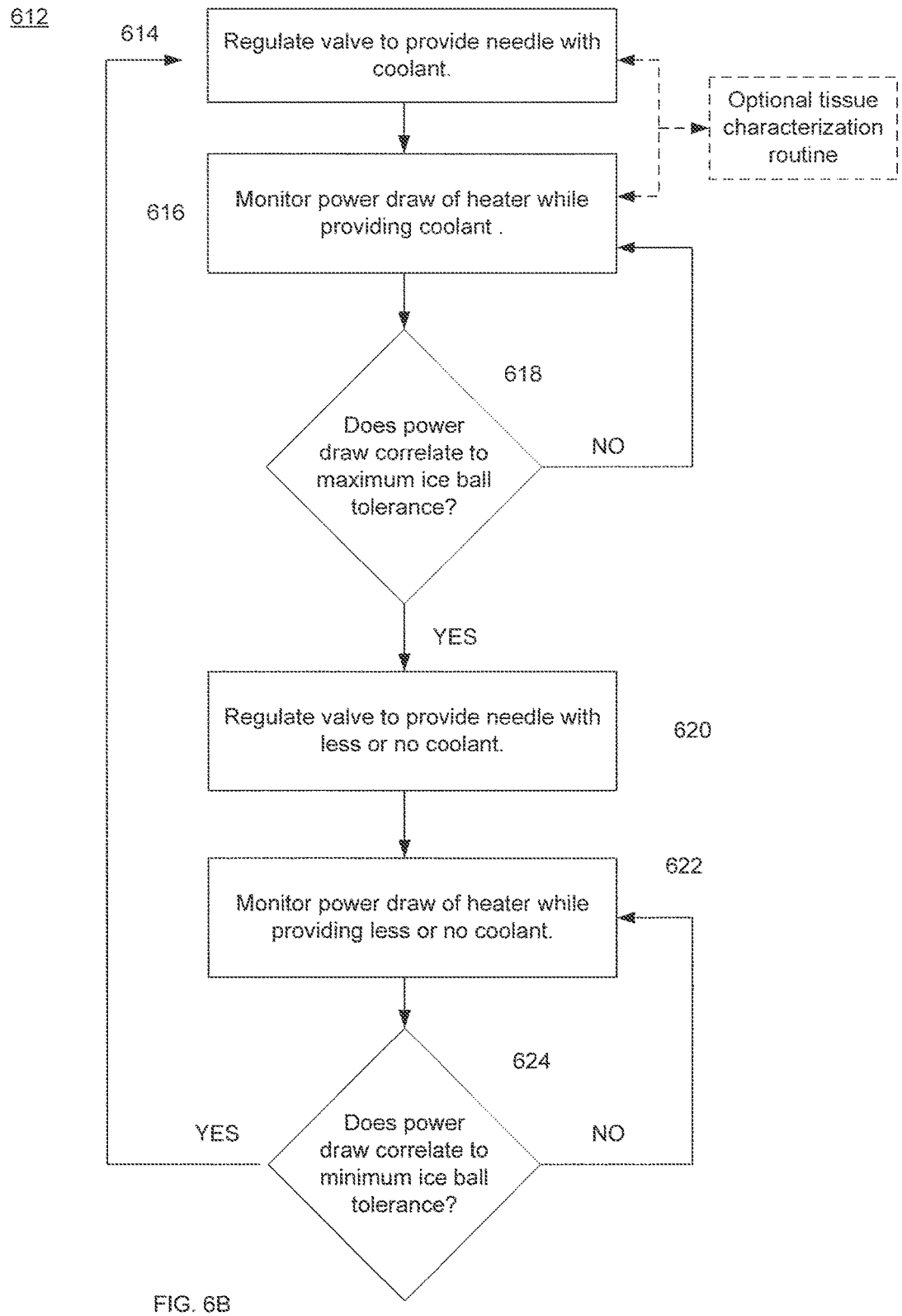
FIG. 6B is a flow chart schematically illustrating a method for treatment using the disposable cryogenic probe and system of FIGS. 1A and 1B, according to an embodiment of the invention.
Figure 6C:
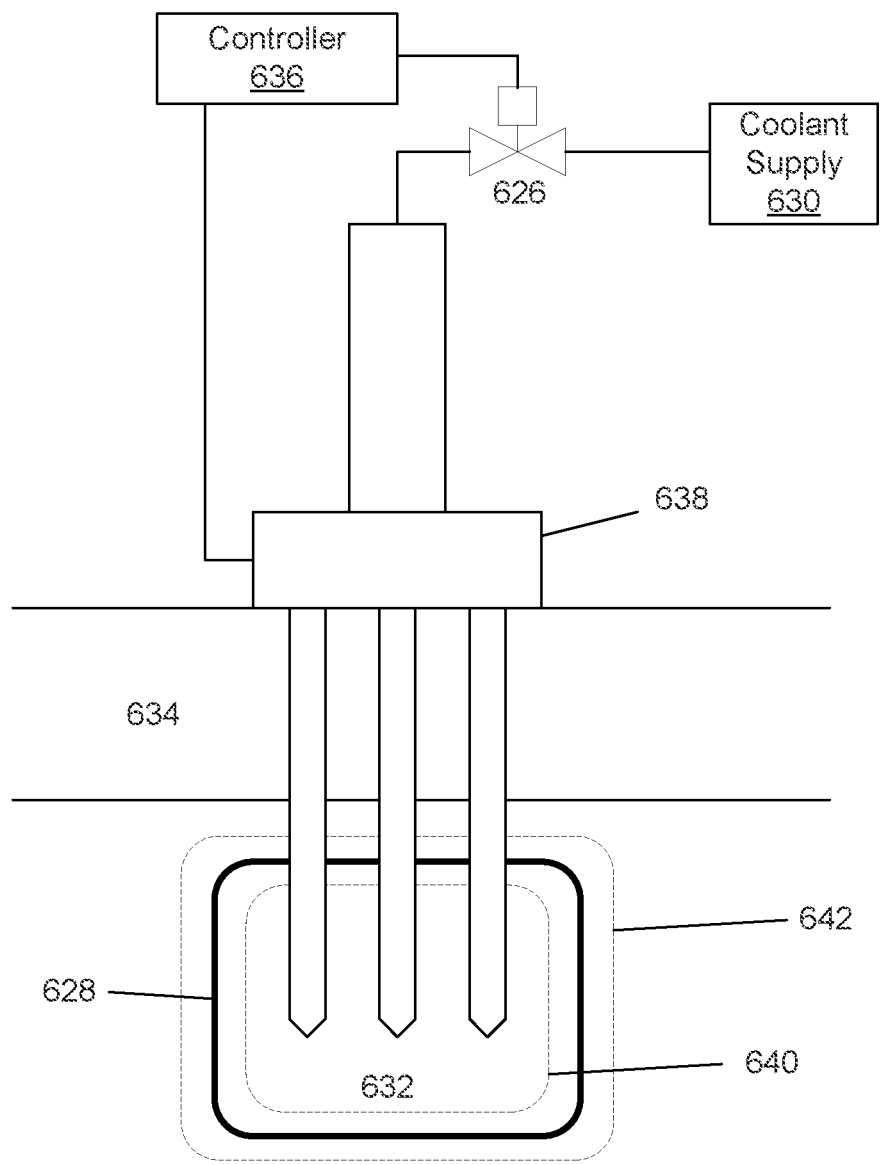
FIG. 6C is a simplified depiction of the method of treatment of FIG. 6B.

FIGS. 6B and 6C show another power monitoring algorithm 612 for regulating a freeze zone, that can be implemented parallel to or in lieu of a treatment algorithm, such as the one shown in FIG. 4, as well as parallel to another power monitoring algorithm, such as the one shown in FIG. 6A. At operation 614, a valve 626 is or has been previously regulated to provide at least one needle with coolant, with the needle being in contact with tissue, as illustrated in FIG. 6C. After some time, a cooling zone 628 forms within the tissue, and will continue to grow in size as long as the needle is supplied with coolant from coolant supply 630. Ideally, cooling zone 628 is limited in size to the area of target tissue 632, to prevent unintentional treatment of non-target tissue 634. While coolant is flowing, power demand from the heater is monitored, which can occur immediately or alternatively after a predetermined amount of time has passed since opening of valve 626.

At operation 618, controller 636 determines whether a sampled power measurement correlates to a maximum ice-ball size desired for a particular therapeutic effect, such as tissue remodeling. Correlations with power draw and cooling zone size can be determined experimentally to determine acceptable power ranges, and the tissue can be pre-characterized according to a tissue characterization algorithm, such as shown in FIG. 6A This measurement may further be correlated according to the time of measurement and temperature of thermally responsive element 638. If the power draw does not correlate with the maximum allowable ice-ball size, then the monitoring is continued.

After a determination that the power demand correlates with the maximum cooling zone size, valve 626 is regulated to provide the needle with less or no coolant at operation 620. After some time cooling zone 628 will decrease in size as heat is drawn in from surrounding tissue. During that time, power supplied to the heater is monitored at operation 622. At operation 624, controller 636 determines whether a sampled power measurement correlates to a minimum ice-ball size required to maintain the desired therapeutic effect. If the power draw does not correlate with the maximum allowable ice-ball size, then the monitoring is continued while cooling zone 628 continues to decrease in size.

Eventually, at operation 624, the power measurement will correspond with the minimum cooling zone size. This causes controller 636 to loop the process and provide more coolant, which causes cooling zone 628 to grow in size. Valve 626 can be metered in this manner to maintain cooling zone 628 within acceptable cooling zone size tolerances (e.g., between lower tolerance 640 and upper tolerance 642), until the procedure is complete.

The methods disclosed herein involve correlating measured parameters to tissue characteristics. An important tissue characteristic is its ability to transfer heat into needle probe(s), or its overall heat transfer rate. The heat transfer rate is a function of the material properties of the tissue (e.g., the thermal conductivity (or the thermal diffusivity which is a function of the thermal conductivity), tissue density, and specific heat capacity) as well as the heat transfer surface area.

Confirming that the cryoprobe is fully inserted into the tissue is important because it confirms that the cooling zone is in the target tissue. A partially inserted cryoprobe can mean that the cryoprobe is within non-target tissue, such as the skin, and thus could cause injury to such non-target tissues. The controller can monitor the power to the heater and detect conditions when the thermally conductive element on the proximal end is not in sufficient thermal contact with the skin to provide protection. This occurs when the skin 'tents' around the shoulder of the thermally conductive element along the needle which limits to some extent the conductive path between the thermally conductive element and skin. When insufficient contact is detected the controller can terminate treatment to reduce possible tissue injury. The controller may also prevent the start of treatment until adequate contact is detected between the skin and thermally conductive element.

Steady state heat transfer between the needle probe(s) and the skin can be described by the following equation $q=UA\Delta T$ where q is the heat transfer rate, U is the overall heat transfer coefficient, A is the heat transfer area and $\Delta T$ is the temperature difference heater block and the skin. The tissue characteristics (including thermal conductivity and thermal diffusivity) are embodied in U and the contacting surface area is also important. It should be noted that this equation describes the steady state heat transfer, however transient conduction includes the same parameters and can be characterized in an analogous manner.

To correlate the relative effectiveness of the heat transfer between the cryoprobe and the tissue, the valve can be opened momentarily to allow cooling of tissue. The temperature change of the heater block could then be monitored over time. A greater temperature change of the heater block indicates lower heat transfer between the tissue and the cryoprobe; a smaller temperature change of the heater block indicates a higher heat transfer rate.

Lower heat transfer levels could be correlated with lower thermal conductivity levels or lower thermal diffusivity levels such as occurs when the needle is inserted in fat. Higher heat transfer rates could be correlated with higher thermal conductivity or thermal diffusivity such as occurs when the needles is inserted in muscle. Lower heat transfer levels could also be correlated with less heat transfer surface area. Since the total contacting surface area of the probe is known, heat transfer rates for a fully inserted needle probe(s) can be characterized. The parameter can be measured when the needle probe is first inserted into the patient tissue to determine whether the needle probe is fully inserted such that the entirety or a predetermined portion of the needle probe is embedded within tissue.

In some embodiments, the tissue characterization process can include turning on the heater and opening the valve. Alternately the heater can be momentarily powered without opening the valve and without cooling. Parameters that can be correlated to tissue characteristics include heater power, the time rate of temperature change of any of a number of temperature sensors, or the instantaneous temperature differential between two temperature sensors (e.g., sensors 52/53) as described below.

A temperature T1 of a first location and a temperature T2 of a second location of the probe, e.g, locations of spacially separated sensors 52/53 can be measured to estimate the heat flux rate described by the equation $q''=(T2-T1)*k/l$, where q" is the heat flux, T2−T1 is the temperature difference, k is the thermal conductivity of the heater block and l is the distance between the two sensors. As disclosed above, higher heat flux rates indicate more heat transfer into the tissue. Alternately, electrical resistance can be measured between the sensors to confirm that the heater block is in contact with the skin.

A variety of target treatment temperatures, times, and cycles may be applied to differing target tissues so as to achieve the desired remodeling. For example, as more fully described in U.S. Patent Publication Nos. 2007/0129714 and 2008/0183164, both previously incorporated herein by reference.

There is a window of temperatures where apoptosis can be induced. An apoptotic effect may be temporary, long-term (lasting at least weeks, months, or years) or even permanent. While necrotic effects may be long term or even permanent, apoptosis may actually provide more long-lasting cosmetic benefits than necrosis. Apoptosis may exhibit a non-inflammatory cell death. Without inflammation, normal muscular healing processes may be inhibited. Following many muscular injuries (including many injuries involving necrosis), skeletal muscle satellite cells may be mobilized by inflammation. Without inflammation, such mobilization may be limited or avoided. Apoptotic cell death may reduce muscle mass and/or may interrupt the collagen and elastin connective chain. Temperature ranges that generate a mixture of apoptosis and necrosis may also provide long-lasting or permanent benefits. For the reduction of adipose tissue, a permanent effect may be advantageous. Surprisingly, both apoptosis and necrosis may produce long-term or even permanent results in adipose tissues, since fat cells regenerate differently than muscle cells.

While the exemplary embodiments have been described in some detail for clarity of understanding and by way of example, a number of modifications, changes, and adaptations may be implemented and/or will be obvious to those as skilled in the art. Hence, the scope of the present invention is limited solely by the claims as follows.

What is claimed is:

1. A system comprising:
a controller;
a cooling supply system having a valve controlled by the controller; and
a needle probe coupled to the controller and configured to receive coolant from the coolant supply system, the needle probe having at least one needle and a heater thermally coupled to the at least one needle;
wherein the controller is configured to:
regulate the coolant to the needle probe using the valve;
provide power to the heater based on power demand from the heater;
monitor the power provided to the heater; and
perform a correlation of the monitored power with at least one of a tissue characteristic and/or an operating parameter;
wherein the heater is further configured to actuate the valve to provide more or less of the coolant to the needle probe based on at least one of the correlated tissue characteristic and/or the operating parameter.

2. The system of claim 1, wherein the power demand of the heater is based on maintaining the heater at a particular temperature.

3. The system of claim 1, wherein the heater is thermally coupled to a thermally conductive element, the thermally conductive element being thermally coupled to a proximal skin engaging portion of the needle.

4. The system of claim 1, wherein the controller is further configured to monitor a temperature of a thermally conductive element coupled to the heater.

5. The system of claim 1, wherein the at least one needle comprises at least one cryogenic sensorless needle.

6. The system of claim 5, wherein the at least one cryogenic sensorless needle is 27 gauge or larger in diameter.

7. The system of claim 1, wherein the at least one needle is 27 gauge or larger in diameter.

8. The system of claim 1, wherein the controller is configured to regulate cooling by operating the valve to provide the coolant to the needle probe for a predetermined period of time.

9. The system of claim 1, wherein the controller is configured to perform the correlation of the monitored power with the operating parameter, wherein the at least one operating parameter comprises at least one of heat transfer rate, heat flux, temperature change rate, or temperature differential.

10. The system of claim 1, wherein the controller is configured to perform the correlation of the monitored power with the tissue characteristic, wherein the tissue characteristic comprises a tissue type.

11. A system comprising:
a controller;
a cooling supply system having a valve controlled by the controller; and
a needle probe coupled to the controller and configured to receive coolant from the coolant supply system, the needle probe having at least one needle and a heater thermally coupled to the at least one needle;
wherein the controller is configured to:
regulate the coolant to the needle probe using the valve;
provide power to the heater based on power demand from the heater;
monitor the power provided to the heater; and
perform a correlation of the monitored power with at least one of a tissue characteristic and/or an operating parameter;
wherein the controller is further configured to provide a user indication based on the correlation of the monitored power with the at least one of the tissue characteristic and/or the operating parameter; and
wherein the user indication comprises a tissue type.

12. The system of claim 11, wherein the regulated coolant to the needle probe forms a cooling zone in a target tissue, the controller further configured to meter the coolant to the needle probe using the valve based on the correlation of the monitored power such that the cooling zone is substantially maintained within an allowable size tolerance.

13. A system comprising:
a controller;
a cooling supply system having a valve controlled by the controller; and
a needle probe coupled to the controller and configured to receive coolant from the coolant supply system, the needle probe having at least one needle and a heater thermally coupled to the at least one needle;
wherein the controller is configured to:
regulate the coolant to the needle probe using the valve;
provide power to the heater based on power demand from the heater;
monitor the power provided to the heater; and
perform a correlation of the monitored power with at least one of a tissue characteristic and/or an operating parameter;
wherein the controller is further configured to provide a user indication based on the correlation of the monitored power with the at least one of the tissue characteristic and/or the operating parameter; and
wherein the user indication comprises needle probe status.

14. The system of claim 13, wherein the controller is further configured to provide a user alert when the needle probe status is unacceptable.

15. A system comprising:
a controller;
a cooling supply system having a valve controlled by the controller; and
a needle probe coupled to the controller and configured to receive coolant from the coolant supply system, the needle probe having at least one needle and a heater thermally coupled to the at least one needle;
wherein the controller is configured to:
regulate the coolant to the needle probe using the valve;
provide power to the heater based on power demand from the heater;
monitor the power provided to the heater; and
perform a correlation of the monitored power with an operating parameter;

wherein the controller is further configured to provide a user indication based on the correlation of the monitored power with the operating parameter; and wherein the operating parameter indicates malfunction of the valve.

16. The system of claim 15, wherein the controller is configured to provide a user alert based on the malfunction.

17. The system of claim 15, wherein the coolant is configured to be regulated by the controller based on a predetermined treatment algorithm and wherein the controller is further configured to modify the treatment algorithm based on the malfunction.

18. A system comprising:
a controller;
a cooling supply system having a valve controlled by the controller; and
a needle probe coupled to the controller and configured to receive coolant from the coolant supply system, the needle probe having at least one needle and a heater thermally coupled to the at least one needle;
wherein the controller is configured to:
regulate the coolant to the needle probe using the valve;
provide power to the heater based on power demand from the heater;
monitor the power provided to the heater; and
perform a correlation of the monitored power with a tissue characteristic, wherein the tissue characteristic comprises a tissue type.

19. The system of claim 18, wherein the controller is configured to adjust an amount of coolant received by the needle probe based on the correlation between the monitored power with the tissue type.

20. The system of claim 18, wherein the tissue type comprises at least one of adipose tissue, nerve, muscle, or fat.

21. A system comprising:
a controller;
a cooling supply system having a valve controlled by the controller; and
a needle probe coupled to the controller and configured to receive coolant from the coolant supply system, the needle probe having at least one needle and a heater thermally coupled to the at least one needle;
wherein the controller is configured to:
regulate the coolant to the needle probe using the valve;
provide power to the heater based on power demand from the heater;
monitor the power provided to the heater; and
perform a correlation of the monitored power with a depth of insertion of the at least one needle and detect insufficient contact with a target tissue based on the correlation.

22. The system of claim 21, wherein the controller is configured to terminate receipt of the coolant by the needle probe when insufficient contact with the target tissue is detected.

23. The system of claim 21, wherein the controller is configured to detect contact between a thermally conductive element coupled to the heater and skin tissue to regulate the coolant to the needle probe.

* * * * *